United States Patent
Rychnovsky et al.

(10) Patent No.: US 7,396,354 B2
(45) Date of Patent: Jul. 8, 2008

(54) LIGHT DELIVERY CATHETER

(76) Inventors: Steven J. Rychnovsky, 524 E. Victoria St. #C, Santa Barbara, CA (US) 93103; John A. Franco, 4560 Horton St. M/S M-564, Emeryville, CA (US) 94608-2916; Jeffrey A. Vasek, 3930 Antone Rd., Santa Barbara, CA (US) 93110; C. T. Lo Blong, 1041- N. 7 St., Lompoc, CA (US) 93436; John S. Hill, 629 Lillebakke Ct., Solvang, CA (US) 93463

( * ) Notice: Subject to any disclaimer, the term of this patent is extended or adjusted under 35 U.S.C. 154(b) by 397 days.

(21) Appl. No.: 10/634,664

(22) Filed: Aug. 5, 2003

(65) Prior Publication Data
US 2004/0093044 A1    May 13, 2004

Related U.S. Application Data

(60) Provisional application No. 60/401,063, filed on Aug. 5, 2002, provisional application No. 60/401,065, filed on Aug. 5, 2002.

(51) Int. Cl.
A61B 18/18    (2006.01)
(52) U.S. Cl. ................... 606/15; 606/7; 607/88
(58) Field of Classification Search ........... 606/7, 606/10–16; 607/88, 89, 92; 600/108, 128–130, 600/156, 175–177; 604/19–21, 508–510, 604/915–921
See application file for complete search history.

(56) References Cited

U.S. PATENT DOCUMENTS

| | | | |
|---|---|---|---|
| 3,045,677 A | 7/1962 | Wallace | 604/101.05 |
| 4,207,874 A | 6/1980 | Choy | 128/6 |
| 4,445,892 A | 5/1984 | Hussein et al. | 604/101 |
| 4,512,762 A | 4/1985 | Spears | 604/21 |
| 4,576,145 A | 3/1986 | Tsuno et al. | |
| 4,619,247 A | 10/1986 | Inoue et al. | 600/116 |

(Continued)

FOREIGN PATENT DOCUMENTS

DE    34 06 294 A    9/1985

(Continued)

OTHER PUBLICATIONS

International Search Report, PCT/US03/24657, Apr. 30, 2004.

(Continued)

*Primary Examiner*—A. Farah
(74) *Attorney, Agent, or Firm*—Bryan Cave LLP

(57) ABSTRACT

The present invention provides improved light delivery catheters for use in therapeutic methods, such as PDT, that require illumination of target tissue within a blood vessel or other hollow body organ. An improved catheter includes an optical fiber that transmits light from a light source at the proximal end of the catheter shaft to a light treatment zone. An occlusion balloon on the distal end of the catheter shaft adjacent to the light treatment zone receives fluid via an inflation lumen in the catheter shaft. An infusion lumen connects with a plurality of infusion ports at the light treatment zone to deliver infusion fluid to the hollow body organ so that blood can be flushed from the region between the light treatment zone and target tissue.

41 Claims, 19 Drawing Sheets

U.S. PATENT DOCUMENTS

| | | | |
|---|---|---|---|
| 4,646,742 A | 3/1987 | Rydell et al. | |
| 4,660,571 A | 4/1987 | Hess et al. | 128/784 |
| 4,685,458 A * | 8/1987 | Leckrone | 606/7 |
| 4,717,387 A | 1/1988 | Inoue et al. | 604/264 |
| 4,784,133 A | 11/1988 | Mackin | 606/7 |
| 4,785,815 A | 11/1988 | Cohen | 128/642 |
| 4,846,172 A | 7/1989 | Berlin | |
| 4,852,567 A * | 8/1989 | Sinofsky | 606/3 |
| 4,878,725 A | 11/1989 | Hessel et al. | 350/96.15 |
| 4,946,460 A | 8/1990 | Merry et al. | 606/24 |
| 5,019,075 A | 5/1991 | Spears et al. | 606/7 |
| 5,028,621 A | 7/1991 | Weishaupt et al. | |
| 5,053,033 A | 10/1991 | Clarke | 606/3 |
| 5,087,244 A | 2/1992 | Wolinsky et al. | 604/53 |
| 5,104,392 A * | 4/1992 | Kittrell et al. | 606/15 |
| 5,108,390 A | 4/1992 | Potocky et al. | 606/21 |
| 5,109,859 A | 5/1992 | Jenkins | 128/662.03 |
| 5,116,317 A | 5/1992 | Carson, Jr. et al. | |
| 5,125,058 A | 6/1992 | Tenerz et al. | 385/66 |
| 5,158,560 A | 10/1992 | Sogawa et al. | 606/15 |
| 5,169,395 A | 12/1992 | Narciso, Jr. | 606/7 |
| 5,176,674 A | 1/1993 | Hofmann | 606/7 |
| 5,178,616 A | 1/1993 | Uemiya et al. | 606/7 |
| 5,188,632 A | 2/1993 | Goldenberg | 606/7 |
| 5,196,005 A | 3/1993 | Doiron et al. | 606/7 |
| 5,201,317 A | 4/1993 | Niwa et al. | |
| 5,217,456 A | 6/1993 | Narciso, Jr. | 606/15 |
| 5,226,889 A | 7/1993 | Sheiban | 604/101 |
| 5,231,684 A | 7/1993 | Narciso, Jr. et al. | 385/80 |
| 5,237,638 A | 8/1993 | Narcisco, Jr. | 385/123 |
| 5,261,904 A * | 11/1993 | Baker et al. | 606/17 |
| 5,267,995 A | 12/1993 | Doiron et al. | 606/15 |
| 5,269,777 A | 12/1993 | Doiron et al. | 606/7 |
| 5,350,375 A | 9/1994 | Deckelbaum et al. | |
| 5,370,608 A | 12/1994 | Sahota et al. | 604/20 |
| 5,409,483 A | 4/1995 | Campbell et al. | |
| 5,417,653 A * | 5/1995 | Sahota et al. | 604/20 |
| 5,441,497 A | 8/1995 | Narciso, Jr. | 606/15 |
| 5,445,608 A | 8/1995 | Chen et al. | |
| 5,454,794 A | 10/1995 | Narciso et al. | 604/280 |
| 5,456,661 A | 10/1995 | Narciso, Jr. | 604/20 |
| 5,466,234 A * | 11/1995 | Loeb et al. | 606/15 |
| 5,505,700 A | 4/1996 | Leone et al. | 604/96 |
| 5,514,092 A | 5/1996 | Stowell et al. | |
| 5,573,531 A * | 11/1996 | Gregory | 606/14 |
| 5,584,872 A * | 12/1996 | LaFontaine et al. | 607/116 |
| 5,588,961 A | 12/1996 | Leone et al. | 604/21 |
| 5,620,438 A | 4/1997 | Amplatz et al. | 606/10 |
| 5,649,923 A * | 7/1997 | Gregory et al. | 606/15 |
| 5,674,198 A | 10/1997 | Leone | 604/101 |
| 5,695,468 A * | 12/1997 | Lafontaine et al. | 604/96.01 |
| 5,700,243 A | 12/1997 | Narciso, Jr. | 604/102 |
| 5,709,653 A | 1/1998 | Leone | 604/20 |
| 5,725,522 A | 3/1998 | Sinofsky | |
| 5,728,068 A | 3/1998 | Leone et al. | 604/101 |
| 5,728,092 A | 3/1998 | Doiron et al. | 606/15 |
| 5,766,151 A | 6/1998 | Valley et al. | |
| 5,797,868 A | 8/1998 | Leone | 604/21 |
| 5,833,682 A | 11/1998 | Amplatz et al. | 606/15 |
| 5,833,688 A | 11/1998 | Oslan et al. | |
| 5,840,059 A | 11/1998 | March et al. | |
| 5,876,426 A | 3/1999 | Kume et al. | 607/88 |
| 5,891,082 A | 4/1999 | Leone et al. | 604/21 |
| 5,899,882 A | 5/1999 | Waksman et al. | 604/96 |
| 5,916,193 A | 6/1999 | Evard et al. | |
| 5,935,075 A | 8/1999 | Bearman et al. | |
| 5,957,917 A * | 9/1999 | Doiron et al. | 606/15 |
| 5,964,751 A | 10/1999 | Amplatz et al. | 606/15 |
| 5,978,541 A | 11/1999 | Doiron et al. | 385/139 |
| 6,010,449 A | 1/2000 | Hansen et al. | |
| 6,013,053 A | 1/2000 | Bower et al. | 604/96 |
| 6,029,671 A | 2/2000 | Stevens et al. | |
| 6,053,911 A | 4/2000 | Ryan et al. | |
| 6,056,721 A | 5/2000 | Shulze | 604/102 |
| 6,086,558 A | 7/2000 | Bower et al. | 604/96 |
| 6,096,030 A | 8/2000 | Ortiz | 604/14 |
| 6,117,128 A | 9/2000 | Gregory et al. | |
| 6,132,423 A | 10/2000 | Aita et al. | 606/7 |
| 6,134,003 A | 10/2000 | Boppart et al. | |
| 6,138,046 A | 10/2000 | Dalton | 600/476 |
| 6,146,409 A | 11/2000 | Overholt et al. | 607/88 |
| 6,165,196 A | 12/2000 | Stack et al. | 606/194 |
| 6,168,594 B1 * | 1/2001 | LaFontaine et al. | 606/41 |
| 6,200,307 B1 | 3/2001 | Van Tassel et al. | |
| 6,322,577 B1 | 11/2001 | McInnes et al. | |
| 6,364,874 B1 | 4/2002 | Bays et al. | 606/15 |
| 6,366,719 B1 | 4/2002 | Heath et al. | 385/31 |
| 6,517,533 B1 | 2/2003 | Swaminathan | 606/20 |
| 6,575,966 B2 * | 6/2003 | Lane et al. | 606/21 |
| 6,923,805 B1 * | 8/2005 | LaFontaine et al. | 606/41 |
| 2001/0037080 A1 | 11/2001 | Mueller et al. | |
| 2002/0045811 A1 | 4/2002 | Feld et al. | |
| 2002/0068294 A1 | 6/2002 | Sinofsky | |
| 2004/0092830 A1 * | 5/2004 | Scott et al. | 600/478 |

FOREIGN PATENT DOCUMENTS

| | | |
|---|---|---|
| DE | 35 12 018 C | 1/1987 |
| EP | 0 311 458 A2 | 12/1989 |
| EP | 0732079 A1 | 9/1996 |
| EP | 07321085 A1 | 9/1996 |
| EP | 0 820 786 A | 1/1998 |
| EP | 1 159 984 A | 12/2001 |
| FR | 2 577 410 A1 | 8/1986 |
| WO | WO 89/06935 | 8/1989 |
| WO | WO 93/15664 A | 8/1993 |
| WO | WO 96/07451 A | 3/1996 |
| WO | WO 97/24154 A | 7/1997 |
| WO | WO 98/48882 A | 11/1998 |
| WO | WO 99/64099 A | 12/1999 |
| WO | WO 01/60427 A | 8/2001 |
| WO | WO 03/079989 A | 10/2003 |

OTHER PUBLICATIONS

Masoud Panjehpour et al, Centering Balloon to Improve Esophageal Photodynamic Therapy, 1992, 663-638, 12:6, Lasers in Surgery and Medicine, Wiley-Liss, Inc., NYC, NY.

International Search Report, PCT/US03/24656 (Sep. 22, 2004).

Y. Uchida, "Coronary Angioscopes that have been Devised in our Laboratories," *Coronary Angioscopy*, 2001—Chapter 2, pp. 7-24.

M. Saab, "Applications of High-Pressure Balloons in the Medical Device Industry", Sep. 2000.

S. Rockson et al, "Photoangioplasty, An Emerging Clinical Cardiovascular Role for Photodynamic Therapy," *Circulation*, 102: 591-596, Aug. 1, 2000.

R.Ginsburg et al., "Percutaneous Transluminal Laser Angioplasty for Treatment of Peripheral Vascular Disease," *Radiology* 1985, 156: 619-24, Sep. 1985.

J. Kaplan et al., "Flash photolysis of Caged Compounds: New Tools for Cellular Physiology," *Trends in Neurocience*, 12: 54-59, Feb. 1989.

C. Gomer et al., "Properties and Applications on Photodynamic Therapy," *Radiation Research*, 120: 1-18, Oct. 1989.

* cited by examiner

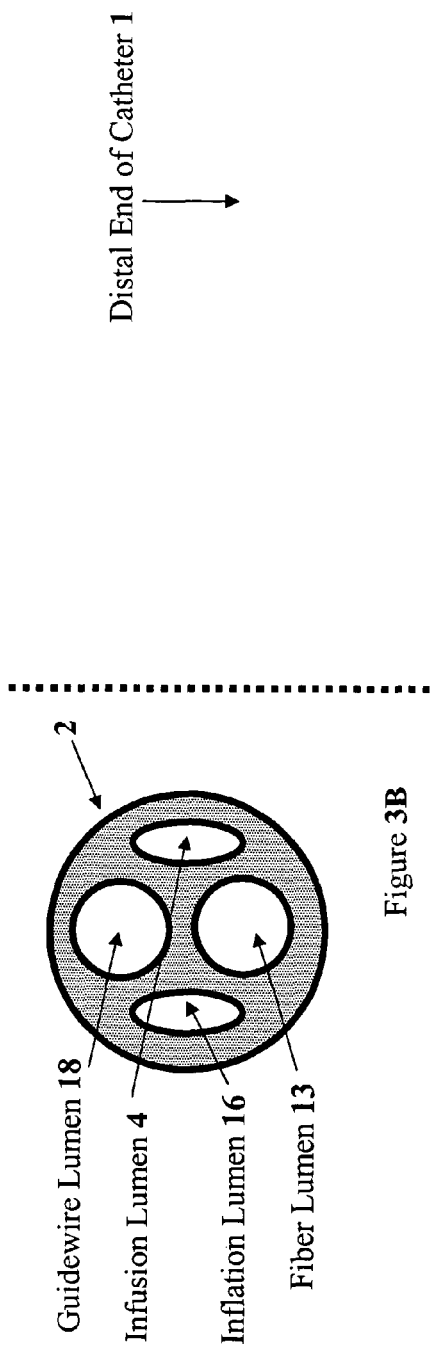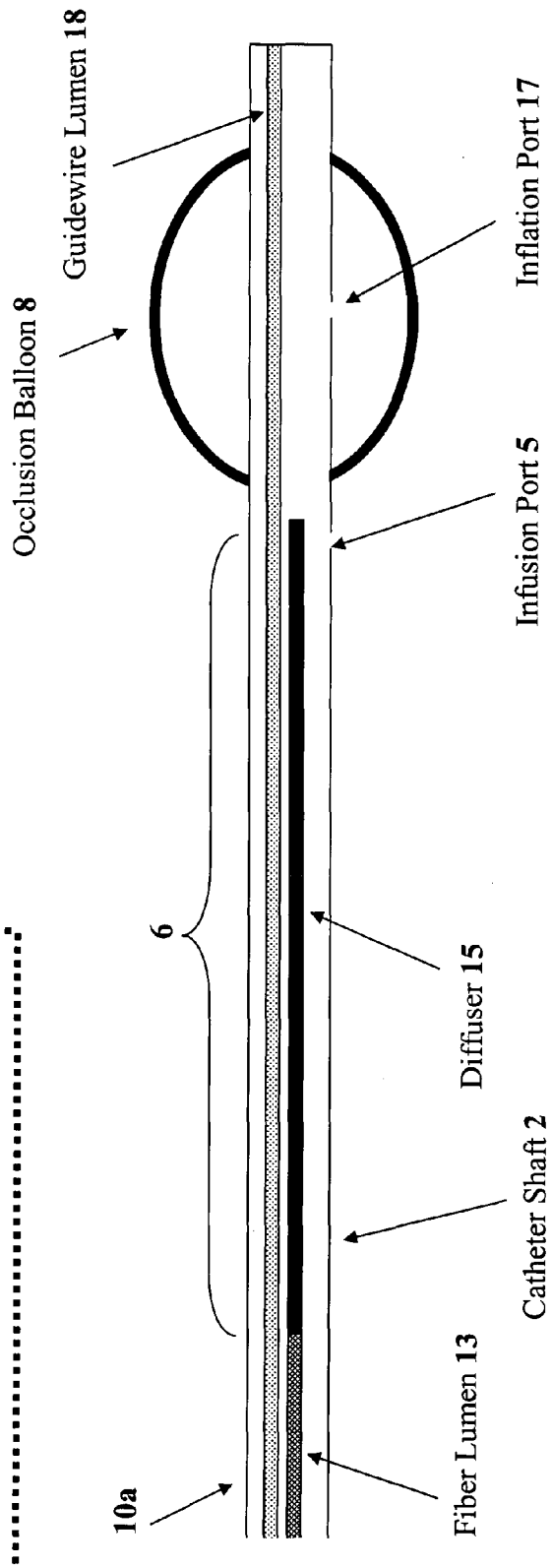
Figure 3A
Figure 3B

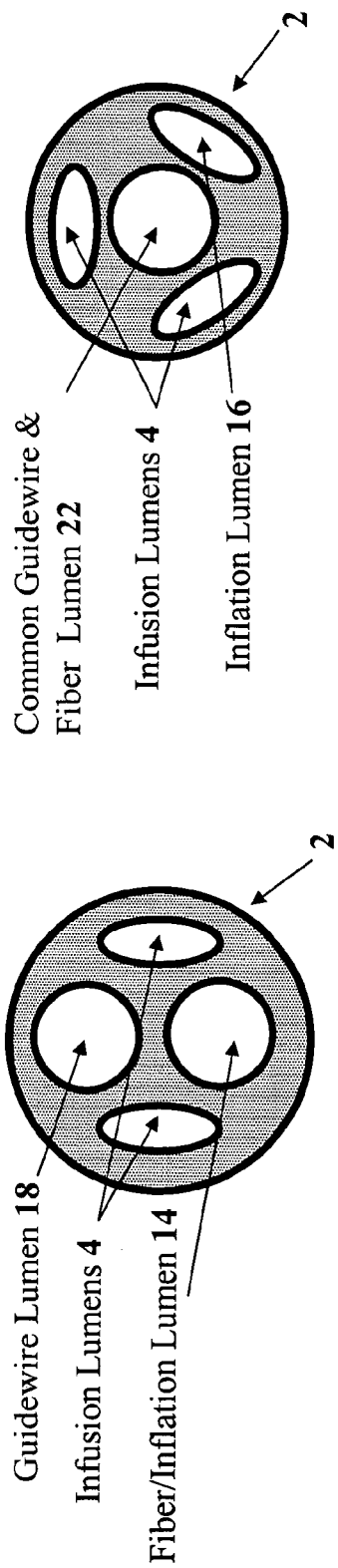
Figure 4A
Figure 4B
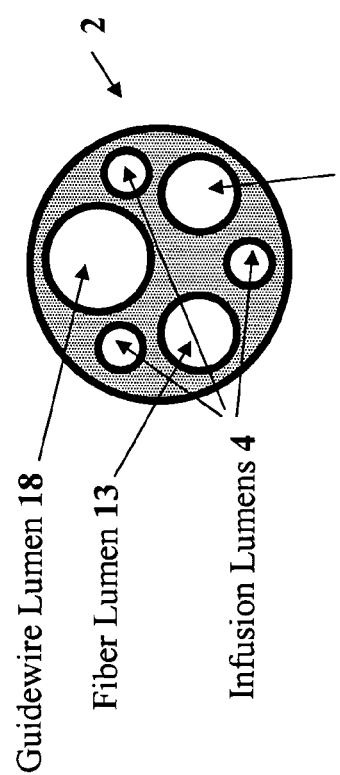
Figure 4C

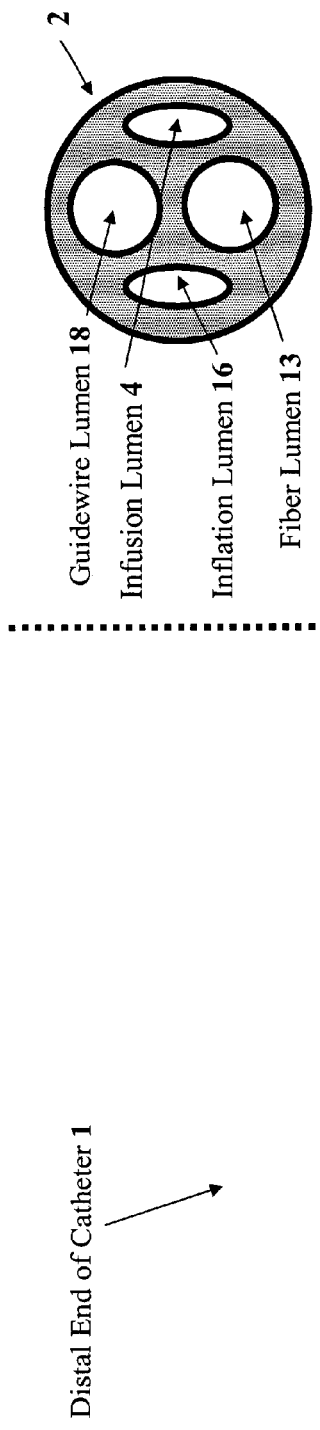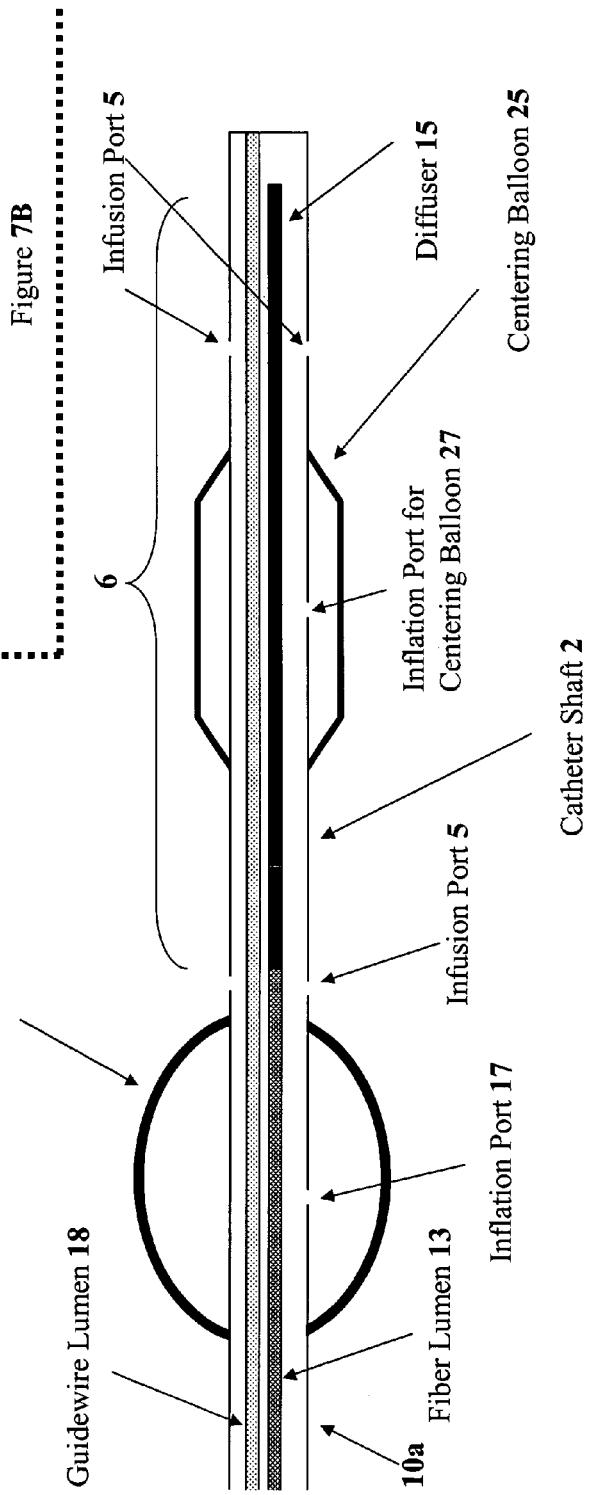
Figure 7B
Figure 7A

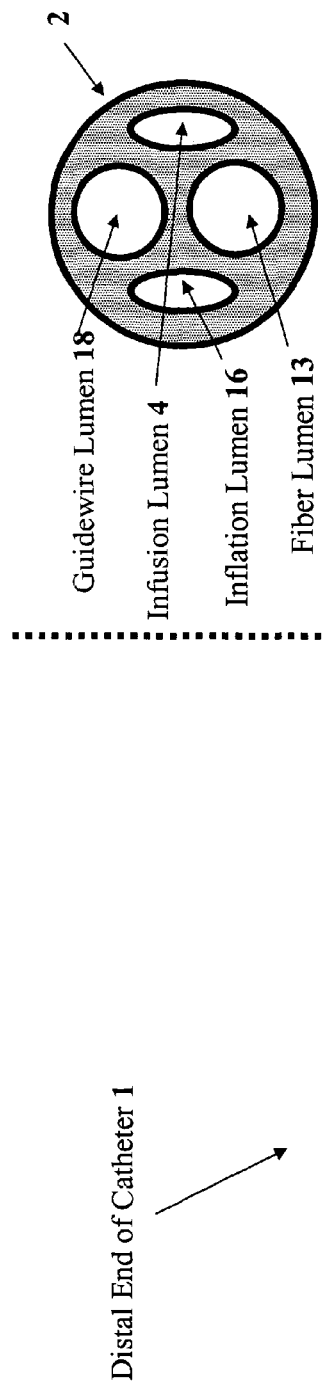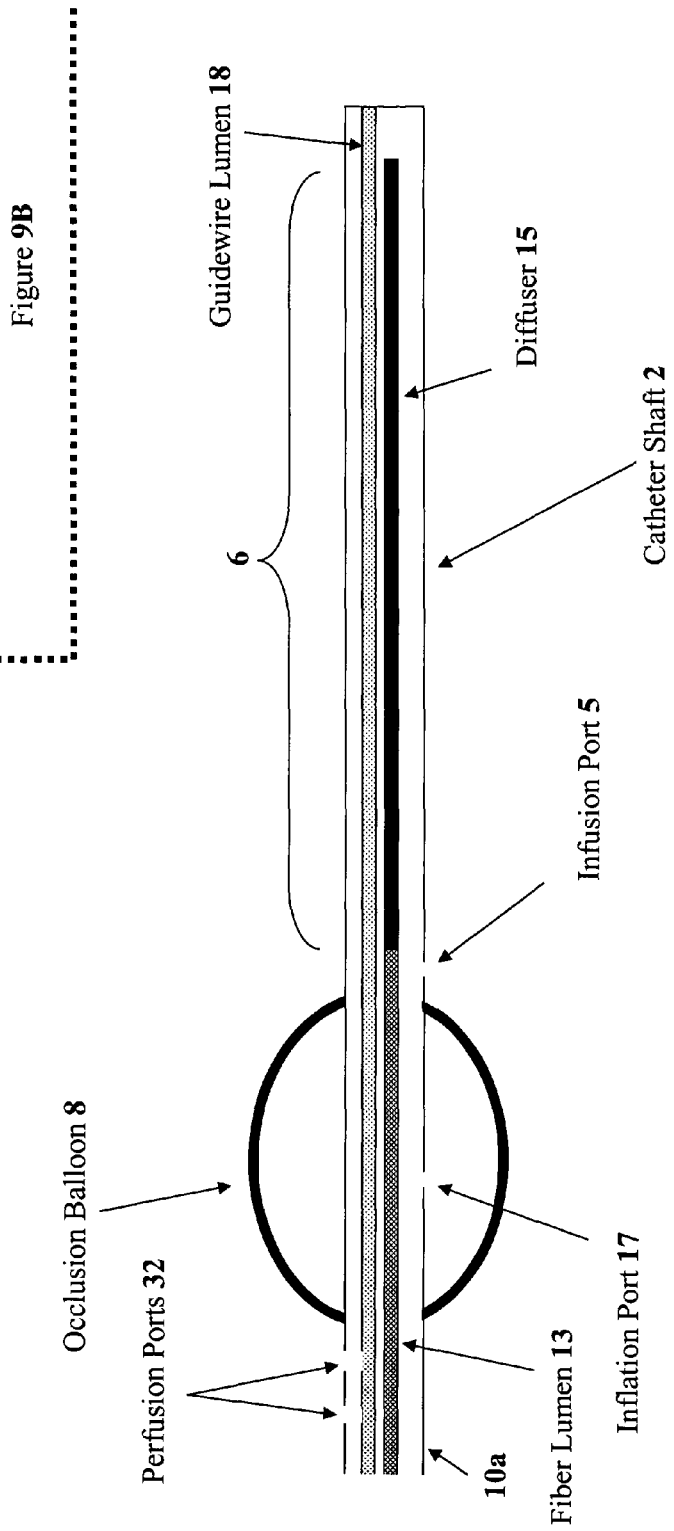
Figure 9A
Figure 9B

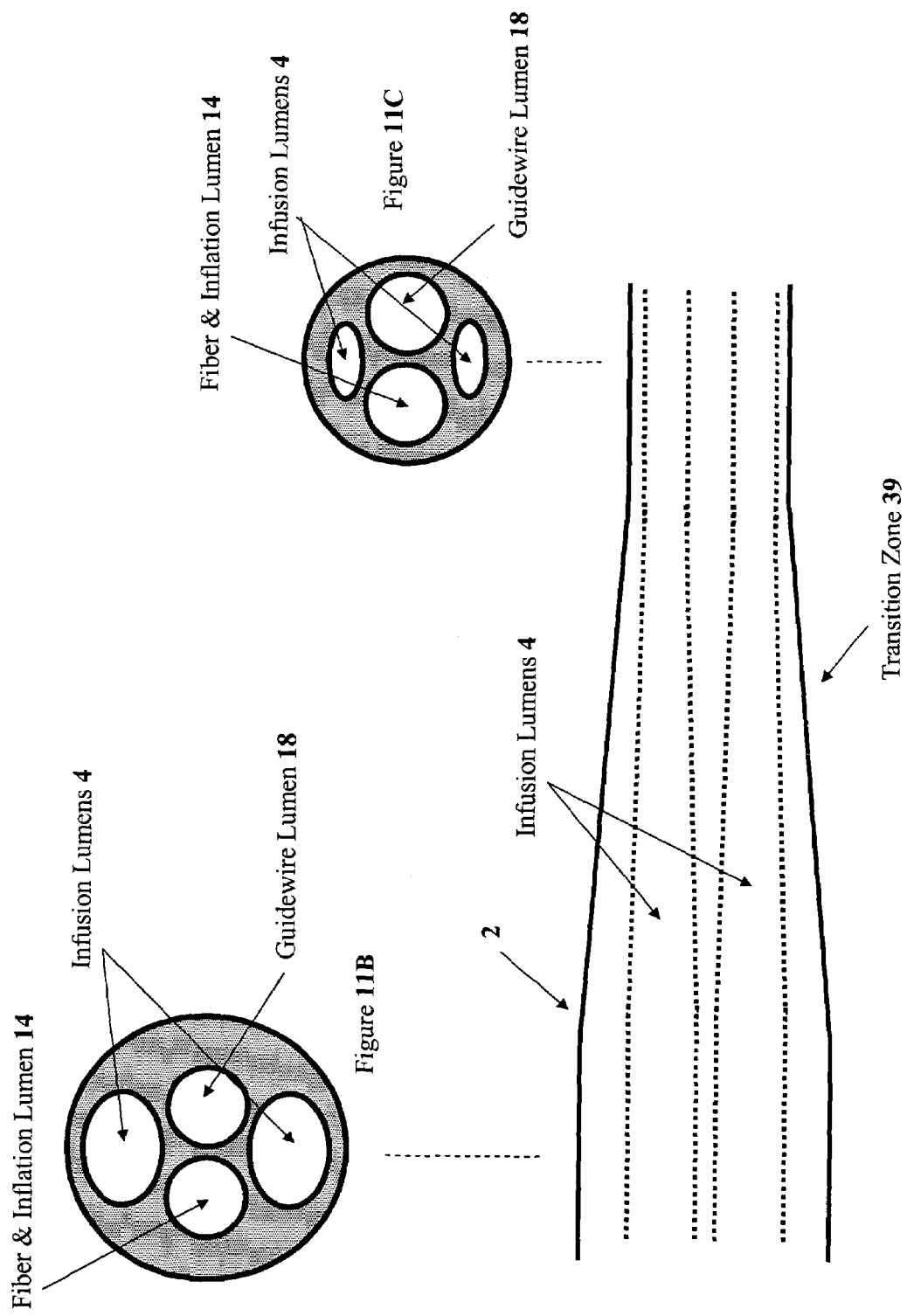

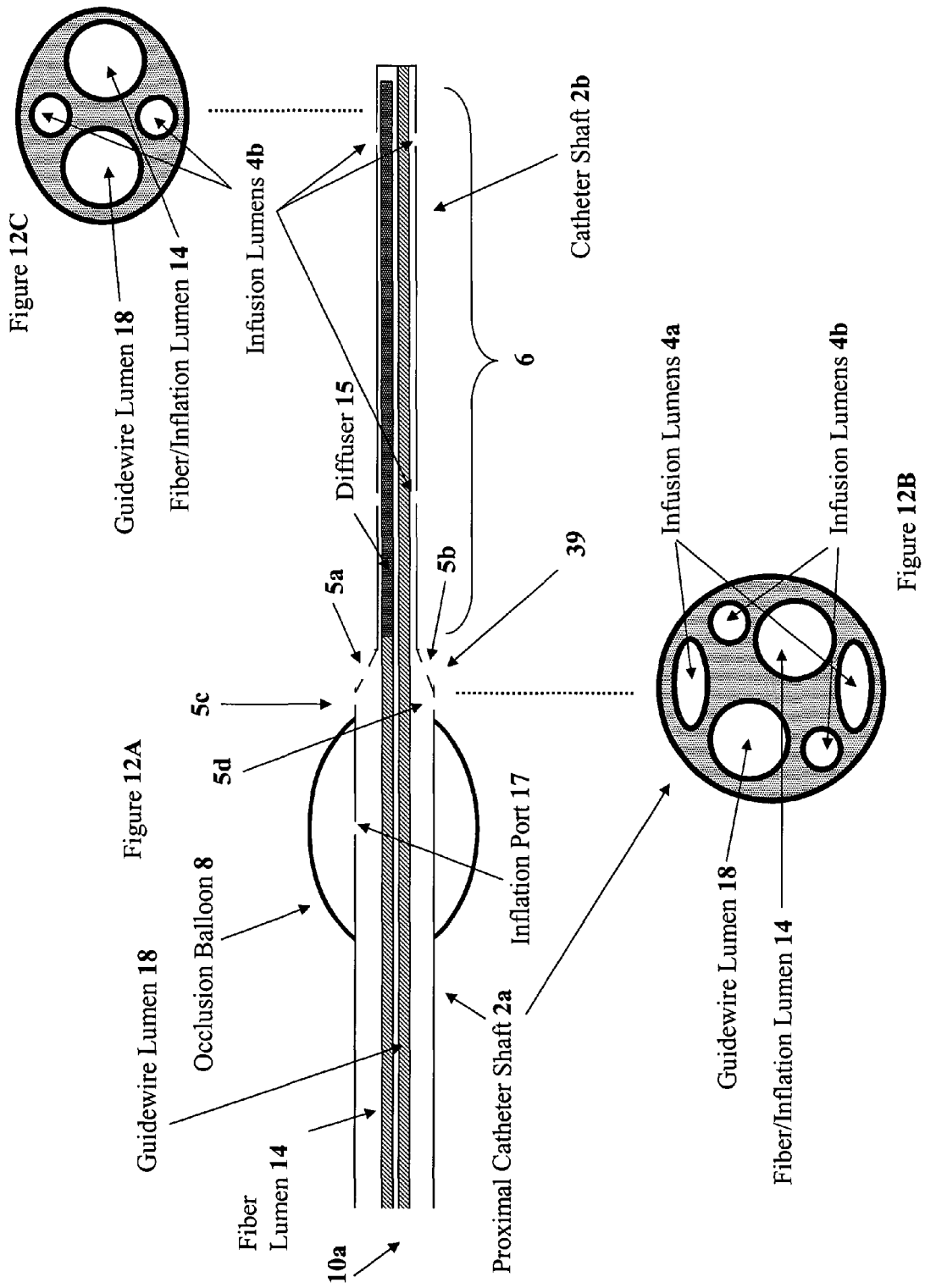

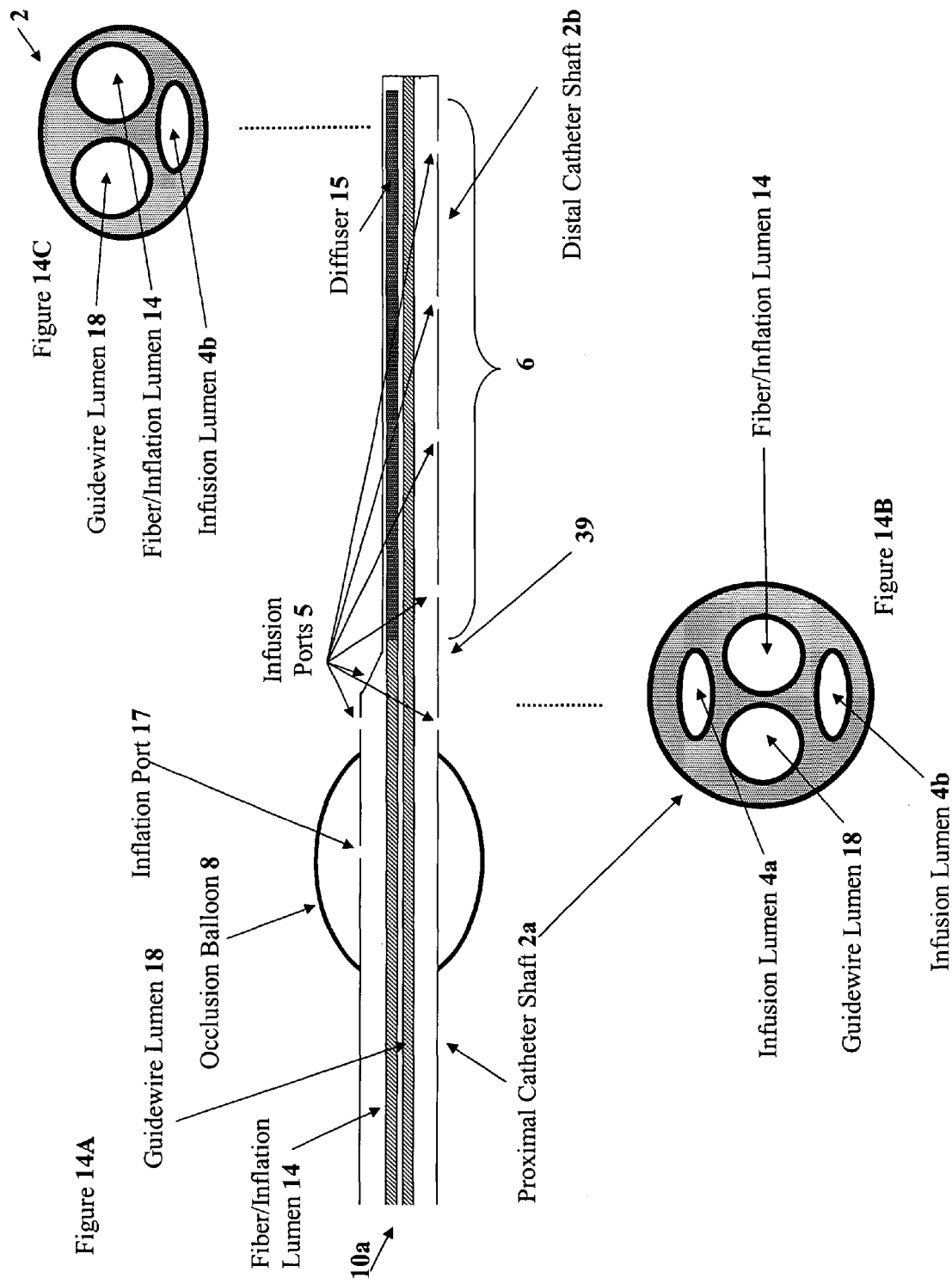

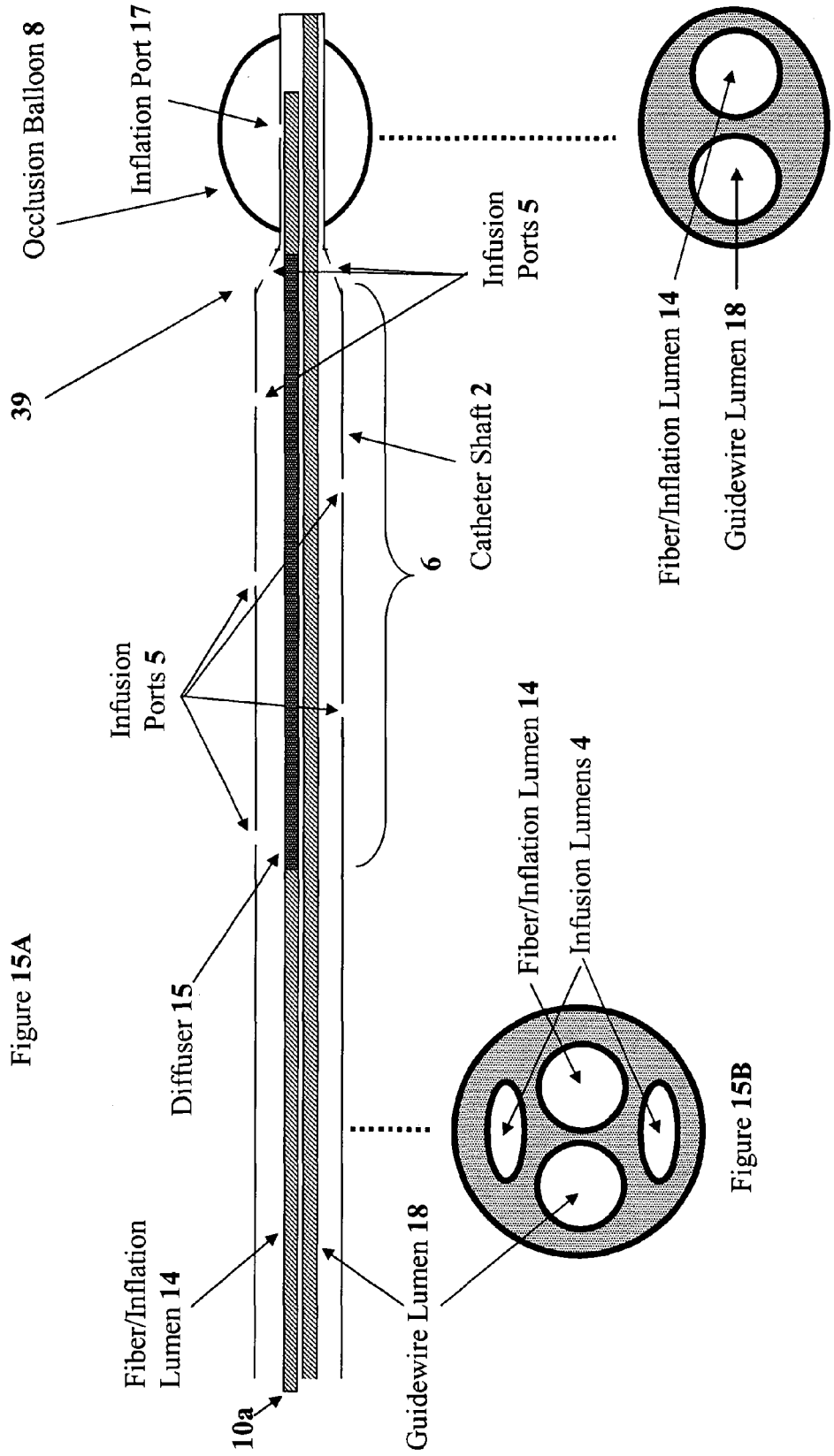

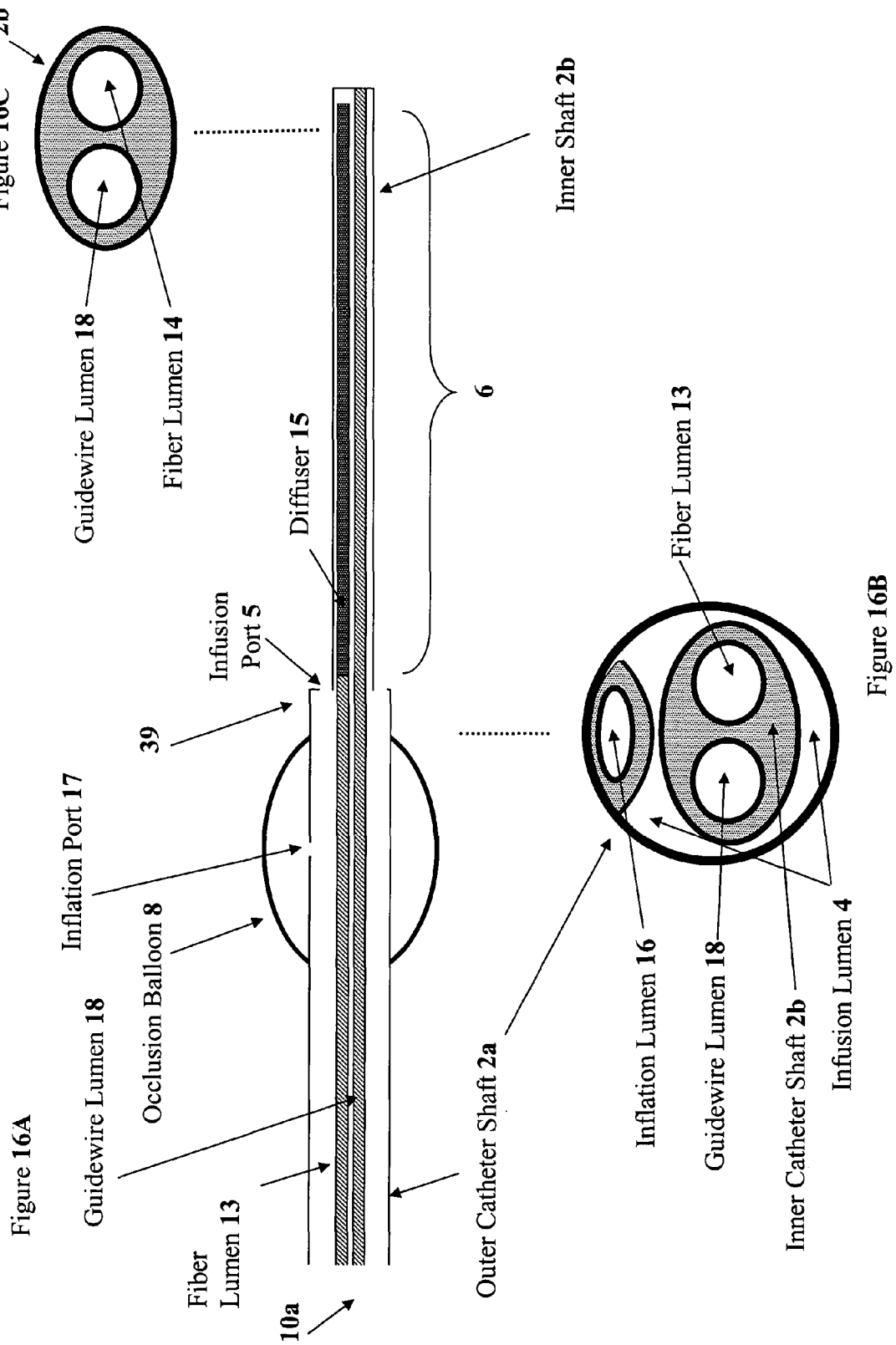

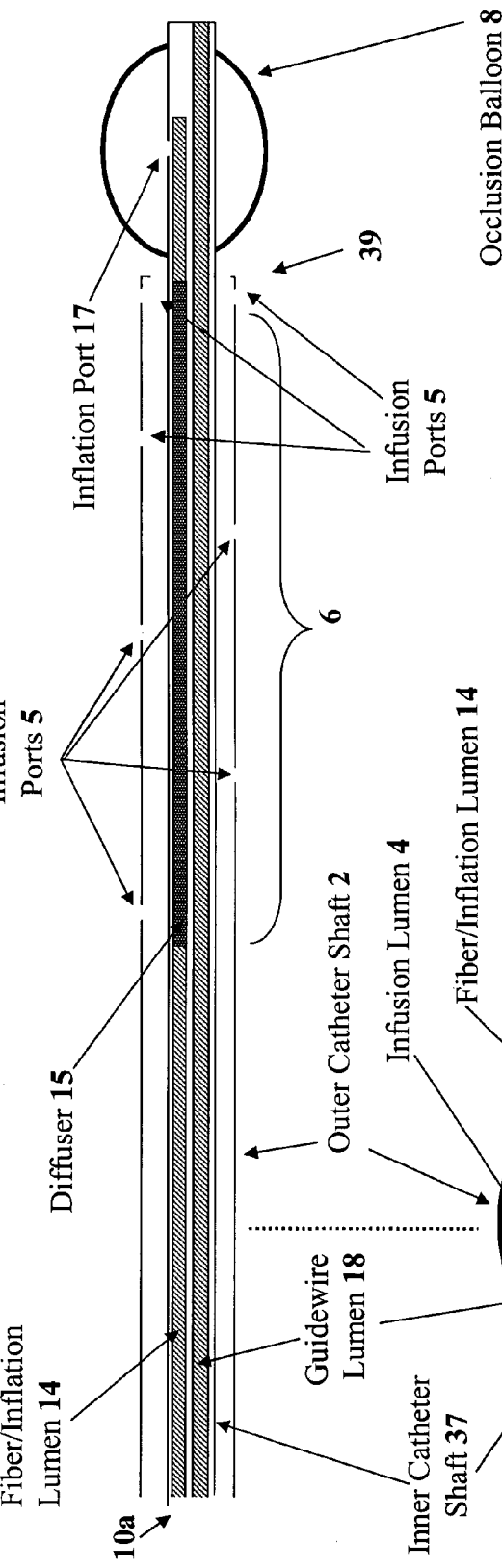
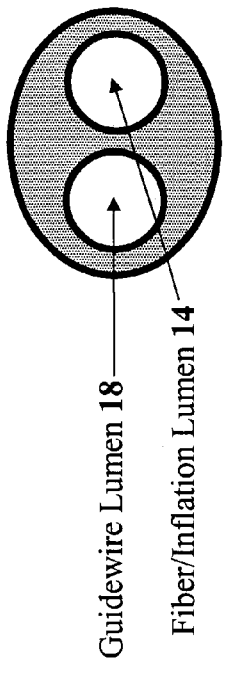
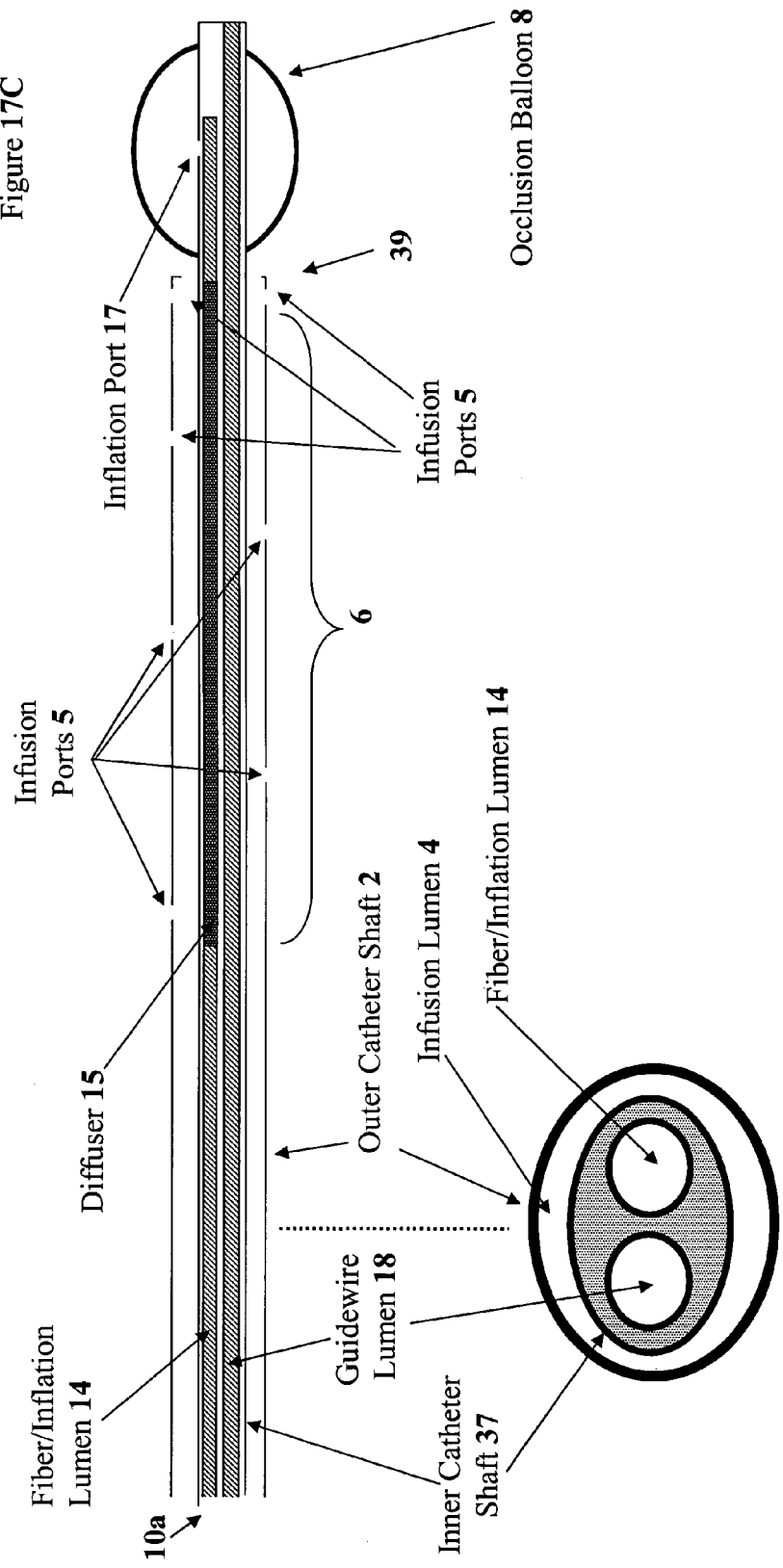
Figure 17A
Figure 17C
Figure 17B

LIGHT DELIVERY CATHETER

CROSS-REFERENCE TO RELATED APPLICATIONS

This application claims the benefit of priority of U.S. Provisional Application No. 60/401,063, filed Aug. 5, 2002, and U.S. Provisional Application No. 60/401,065, filed Aug. 5, 2002.

FIELD OF THE INVENTION

The invention relates to the field of medical instruments used in administering light for therapeutic methods, such as photodynamic therapy (PDT), that require light illumination of target tissue. The present invention provides improved light delivery catheter devices that provide more uniform light delivery by more effectively flushing blood from the light treatment site, as well as other features and advantages.

BACKGROUND

PDT is a medical treatment that utilizes light activated photosensitive dyes to elicit a beneficial biological response. These dyes, or photosensitizers, elicit a biological response when irradiated with light within a certain wavelength range but are inert without such illumination.

A promising area for the application of PDT is in the treatment of cardiovascular disease indications such as vulnerable plaque, atherosclerosis and restenosis. Such applications generally involve the delivery of photosensitizers into a blood vessel to be treated, followed by the delivery of light to the target tissue, often through a light delivery catheter. One of the challenges associated with PDT and other treatments employing endovascular light delivery arises from the tendency of blood to attenuate light in the treatment region. The PDT effect can be significantly degraded if blood is not eliminated from the light path. This adverse effect exists for PDT methods utilizing all wavelengths of light treatment, but is particularly significant for treatments using short wavelengths of light (e.g., less than 610 nm), where light attenuation by blood is most significant.

Balloon catheters have been used in an effort to eliminate blood during the light delivery process. A commonly employed approach is to place a light-emitting fiber within a transparent or translucent angioplasty-style balloon. Blood is removed from the light treatment region by inflating the balloon to displace the blood. This approach has been employed almost exclusively for most cardiovascular PDT methods.

For example, Spears, U.S. Pat. No. 4,512,762, discloses a balloon catheter equipped with flexible optical fibers for transmission of light from an external source for illumination of the interior of the inflated balloon. By inflation of the balloon, the blood between the balloon and the diseased vascular wall is displaced. Other examples of PDT catheters employing an optical element within a displacement balloon include the following: Narciso, U.S. Pat. Nos. 5,169,395; 5,441,497; 5,700,243; Leone, U.S. Pat. Nos. 5,797,868; 5,891,082; EP 0 732 085; EP 0 732 079; Ligtenberg et al., EP 0 732 079 A1; Bower et al., U.S. Pat. Nos. 6,013,053; 6,086, 558; Overholt et al., U.S. Pat. No. 6,146,409; Aita et al., U.S. Pat. No. 6,132,423; and Amplatz et al., U.S. Pat. No. 5,620, 438.

A significant problem with the displacement balloon approach described in the foregoing patents is that it fails to fully displace the blood, leaving some blood trapped between the outside surface of the inflated balloon and the inside surface of the vascular wall. With this approach, adequate displacement generally requires a balloon that is at least as long as the light treatment zone. To achieve a cylindrical shape that is consistent with the shape of the vessel being treated, non-compliant balloon materials are typically used, because balloons made from such materials retain their shape when inflated. To avoid injuries associated with mechanical trauma due to inflation of a non-compliant cylindrically-shaped balloon, it is necessary to inflate the balloon using a very low pressure. However, such a balloon inflated at low pressure usually cannot exert sufficient force to adequately displace the surrounding blood. Consequently, the angioplasty balloon can at best be a compromise solution since under-inflation prevents mechanical trauma without achieving adequate blood removal, whereas over-inflation achieves better blood removal but with increased risk of mechanical trauma.

One attempt to overcome this shortcoming of the angioplasty design approach is to utilize a so-called "weeping balloon" as described in Kume et al., U.S. Pat. No. 5,876,426; Leone, U.S. Pat. No. 5,709,653; and Amplatz et al., U.S. Pat. Nos. 5,833,68 and 5,964,751. Each of these patents discloses a light delivery catheter fitted with a porous angioplasty-style balloon that leaks fluid from its surface to flush blood from around the periphery of the balloon. Though such weeping balloons may provide better blood elimination than standard angioplasty-style balloons, they suffer from some significant shortcomings. For example, flushing fluid delivered in such a manner tends to find the path of least resistance to escape into the open blood vessel, leaving pockets of blood trapped between the balloon and the vessel wall. Another limitation is that when the balloon is deflated blood can be sucked into the balloon where it will attenuate light delivered in subsequent inflation and treatment cycles.

Other shortcomings of both the standard displacement balloon and the weeping balloon approaches can arise from the use of non-compliant balloon materials. Each of the patents referenced above generally discloses a light delivery catheter having an elongated, tubular balloon that extends along the length of the catheter at least as long as the length of the light treatment zone. As explained by Saab, in "Applications of High-Pressure Balloons in the Medical Device Industry," published in *Medical Device and Diagnostic Industry*, September 2000, pg. 86, achieving this tubular shape in an inflated balloon generally requires the use of a relatively non-compliant (i.e., less elastic) balloon material that will retain its shape when inflated. Because non-compliant balloons are more rigid and do not conform to the shape of the vessel, such balloons have a greater tendency to cause mechanical trauma to the vessel. The resulting injury response can lead to restenosis.

The non-compliant angioplasty balloon is also limited in its ability to treat long tortuous vessels. When using a light emitting element within an angioplasty balloon it is necessary to fully inflate the balloon to adequately displace blood. However, this can be difficult in tortuous vessels, especially if the treatment length is greater than 1-2 cm. This is due to the fact that, when inflated, the non-compliant angioplasty balloon tends to inflate in a straight line, rather than follow the curvature of the vessel. The result is that the balloon tends to straighten the vessel, causing mechanical trauma to the vessel.

The non-compliant angioplasty balloon also has a limited ability to treat small diameter vessels. When using the angioplasty balloon approach, it is necessary to mount the non-compliant angioplasty balloon on the catheter shaft overlapping the light treatment zone. However, use of such a non-compliant balloon adds to the diameter of the device in the treatment zone, thereby limiting access to small vessel diameters.

Still another shortcoming of the non-compliant angioplasty balloon is in the treatment of vessels whose diameter tapers or otherwise changes within the length of the section to be treated. When using an angioplasty style balloon it is necessary to inflate the balloon to displace the blood. This can cause injury within the smaller diameter regions of the vessel being treated since these balloons generally have a constant diameter along their length.

Furthermore, non-compliant balloon devices have a limited ability to treat multiple vessel diameters with a single device. With the angioplasty balloon approaches, the device generally must be correctly sized to the vessel to be treated. This requires that a significant stock of devices be kept on hand and also limits the various vessel geometries that can be treated.

Thus, there is a significant need for improved light delivery catheters that can provide improved blood elimination along the light treatment region and can avoid the shortcomings associated with prior devices employing non-complaint angioplasty balloons. The present invention provides improved light delivery catheters having these and other features and advantages.

SUMMARY

The present invention provides improved light delivery catheters for use in therapeutic methods, such as PDT, that require illumination of target tissue within a blood vessel or other hollow body organ. An improved catheter comprises a catheter shaft having a light treatment zone at its distal end. A light guide, such as an optical fiber, in the catheter shaft transmits light from a light source at the proximal end of the catheter shaft to the light treatment zone. An occlusion balloon is positioned on the distal end of the catheter shaft adjacent to the light treatment zone. An inflation lumen in the catheter shaft, and in fluid communication with the balloon, delivers fluid from an inflation fluid source at the proximal end of the catheter shaft to the balloon. An infusion lumen in the catheter shaft delivers infusion fluid from an infusion fluid source at the proximal end of the catheter shaft to the light treatment zone. A plurality of infusion ports formed on the light treatment zone, and in fluid communication with the infusion lumen, deliver infusion fluid to the hollow body organ so that blood can be flushed from the region between the light treatment zone and target tissue.

The invention also provides light delivery catheters having features to allow detection of emitted light. In one embodiment, the catheter has a light delivery optical fiber having a distal end terminating in the light treatment zone. A second light detection optical fiber in the catheter shaft detects light emitted by the first optical fiber and transmits the detected light to the proximal end of the catheter shaft. In another embodiment, a fluorescent material is incorporated into the distal end of the catheter shaft to provide a fluorescent emission when exposed to light emitted from the optical fiber. This emission can propagate back to the proximal end of the optical fiber to allow monitoring of light delivery.

Another aspect of the invention provides improved infusion lumens for use with light delivery catheters. In one embodiment, the infusion lumen has a larger diameter at the proximal end of the catheter than at the distal end. The transition between the larger and smaller diameter generally occurs at the distal end of the catheter, proximal to the light treatment zone. This approach allows much higher flow rates to be achieved for a given pressure than would otherwise be possible if the diameter of the infusion lumens near the proximal end were the same as those near the distal end, where the shaft diameter is relatively small.

DRAWINGS

These and other features, aspects and advantages of the present invention will become more fully apparent from the following detailed description, appended claims, and accompanying drawings where:

FIG. 1A schematically illustrates a side view of the distal end of a light delivery catheter;

FIG. 1B is a cross-sectional view of the light delivery catheter of FIG. 1A, with the plane of the cross-section coincident with the location on the shaft were discrete flush ports have been created on the periphery of the shaft;

FIG. 2 schematically illustrates a side view of the proximal end of the light delivery catheter of FIG. 1A;

FIG. 3A schematically illustrates a side view of a backflush embodiment of a light delivery catheter;

FIG. 3B is a cross-sectional view of the light delivery catheter of FIG. 3A;

FIG. 4A schematically illustrates a shaft cross-section of an embodiment of a light delivery catheter where fiber and guidewire are adjacent to each other;

FIG. 4B schematically illustrates a shaft cross-section of an embodiment of a light delivery catheter in which a single lumen is used for both fiber and guidewire;

FIG. 4C schematically illustrates a shaft cross-section of an embodiment of a light delivery catheter in which three infusion lumens are oriented at 120 degrees around the periphery of the catheter shaft;

FIG. 5A schematically illustrates a side view of a light delivery catheter having a rapid exchange guidewire port proximal to the light treatment zone;

FIG. 5B is a cross-sectional view of the light delivery catheter of FIG. 5A;

FIG. 6A schematically illustrates a side view of a light delivery catheter having a rapid exchange guidewire port distal to the light treatment zone;

FIG. 6B is a cross-sectional view of the light delivery catheter of FIG. 6A in the region proximal to the rapid exchange port;

FIG. 7A schematically illustrates a side view of a light delivery catheter having a centering balloon over the light treatment zone;

FIG. 7B is a cross-sectional view of the light delivery catheter of FIG. 7A;

FIG. 8A schematically illustrates a side view of a light delivery catheter having an angioplasty balloon over the light treatment zone;

FIG. 8B is a cross-sectional view of the light delivery catheter of FIG. 8A;

FIG. 9A schematically illustrates a side view of a light delivery catheter having perfusion ports;

FIG. 9B is a cross-sectional view of the light delivery catheter of FIG. 9A;

FIG. 10A schematically illustrates a side view of a light delivery catheter having a fiber for light detection;

FIG. 10B is a cross-sectional view of the light delivery catheter of FIG. 10A;

FIG. 11A schematically illustrates a side view of a tapering catheter shaft design;

FIG. 11B is a cross-sectional view of the light delivery catheter of FIG. 11A proximal to the transition;

FIG. 11C is a cross-sectional view of the light delivery catheter of FIG. 11A distal to the transition;

Figure 13A:
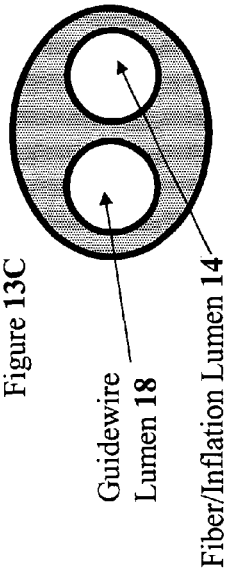
Figure 13C:
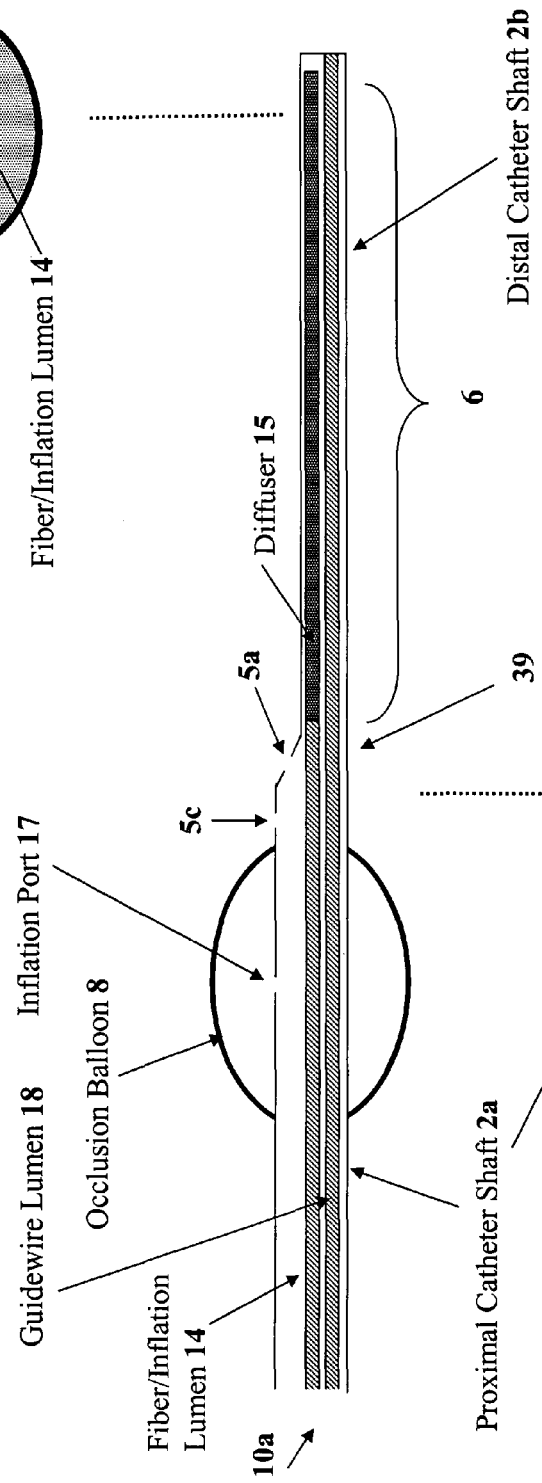
Figure 13B:
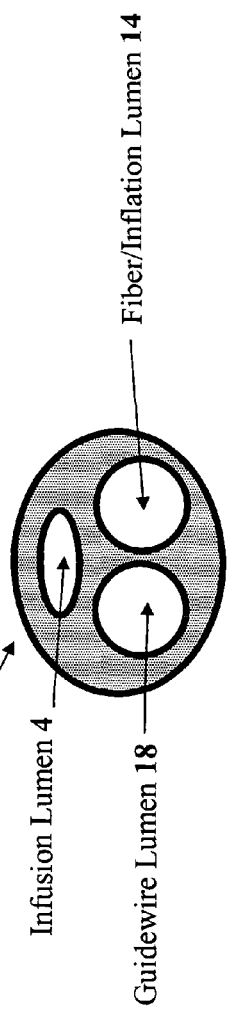
Figure 18:
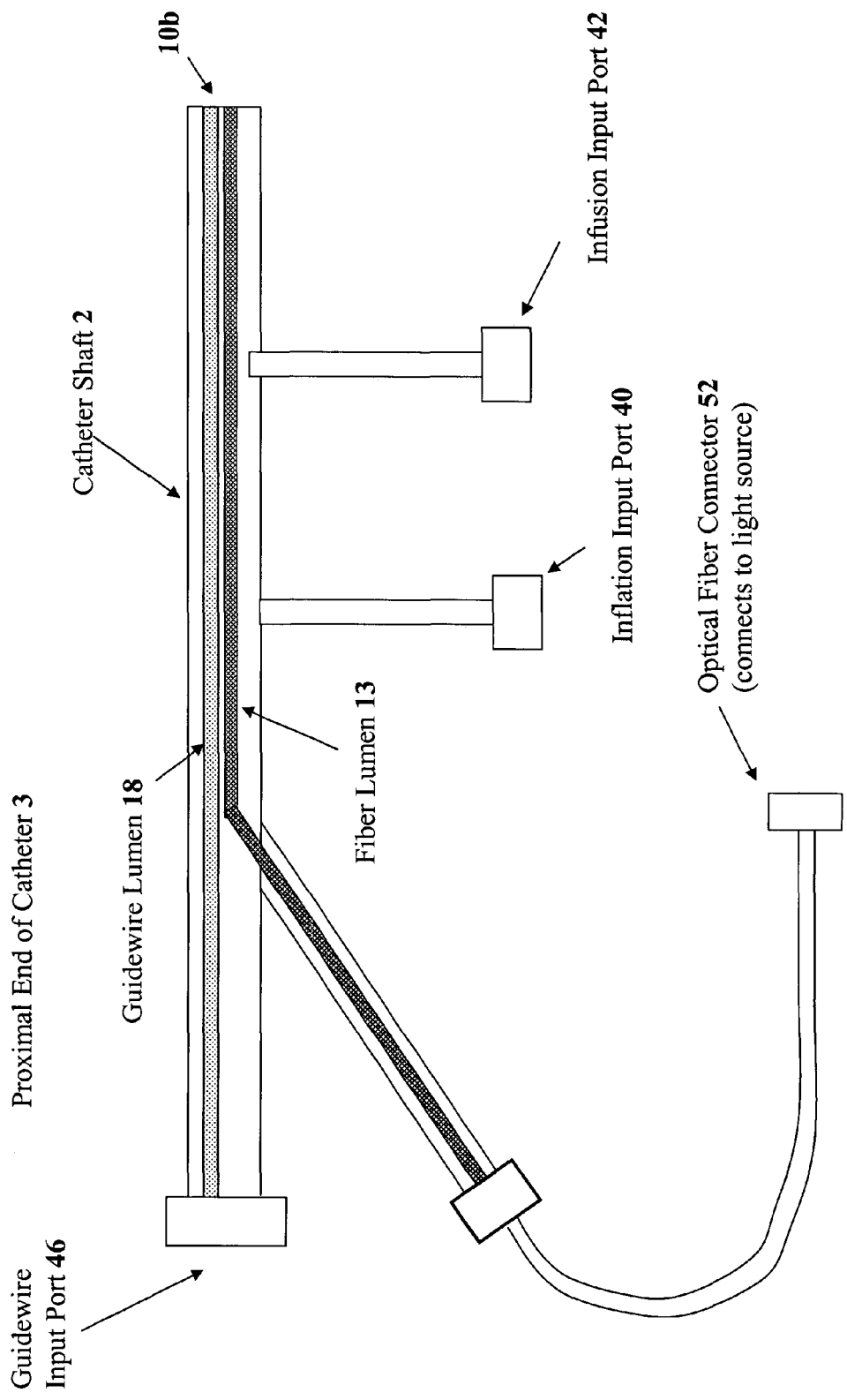
Figure 19:
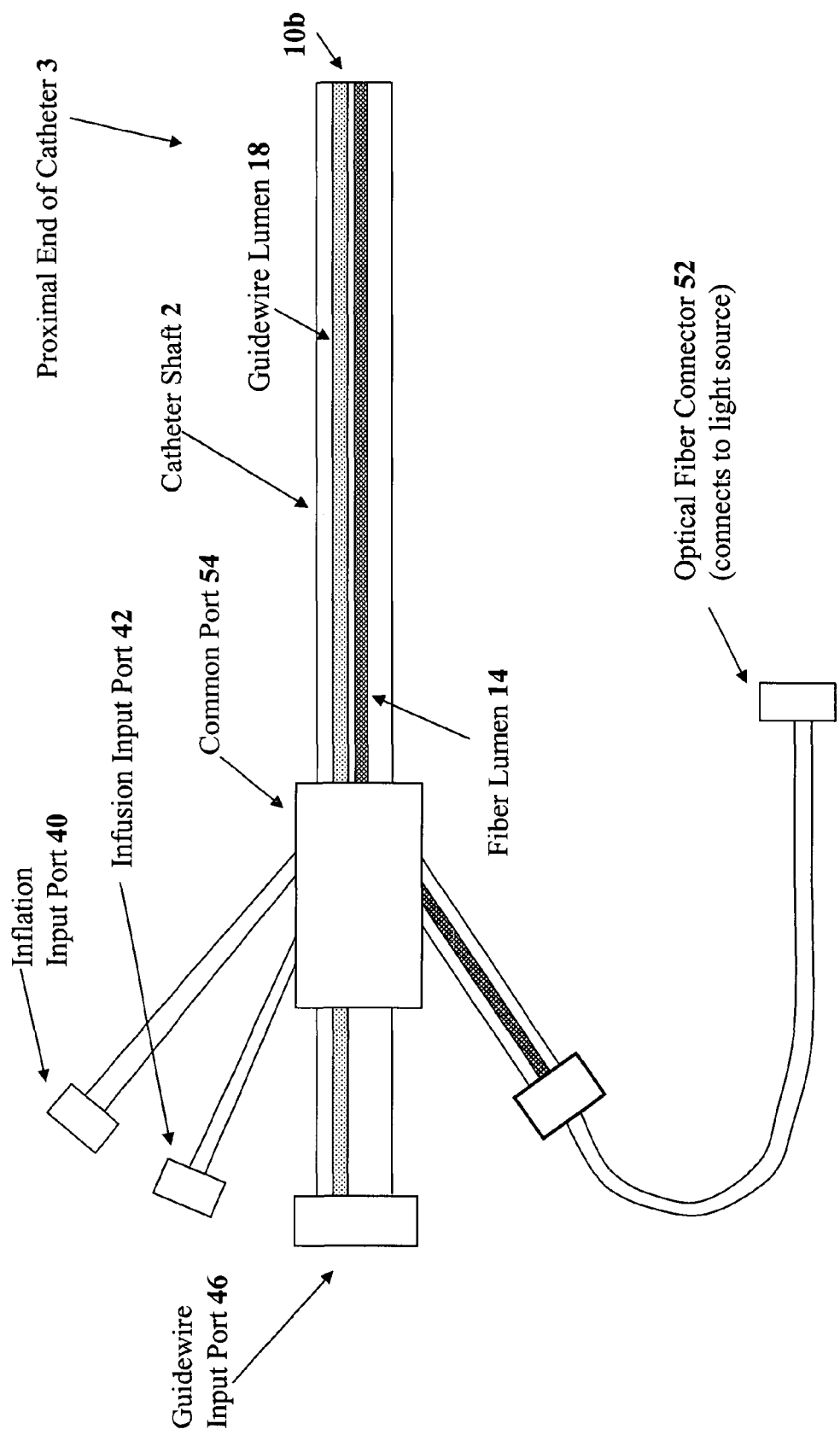

FIG. 12A schematically illustrates a side view of a light delivery catheter having infusion lumens terminating in infusion ports proximal to the light delivery zone;

FIG. 12B is a cross-sectional view of the light delivery catheter of FIG. 12A proximal to the transition;

FIG. 12C is a cross-sectional view of the light delivery catheter of FIG. 12A distal to the transition;

FIG. 13A schematically illustrates a side view of another embodiment of a light delivery catheter having infusion lumens terminating in infusion ports proximal to the light delivery zone;

FIG. 13B is a cross-sectional view of the light delivery catheter of FIG. 13A proximal to the transition;

FIG. 13C is a cross-sectional view of the light delivery catheter of FIG. 13A distal to the transition;

FIG. 14A schematically illustrates a side view of a light delivery catheter having one infusion lumen terminating proximal to the light treatment zone and a second infusion lumen continuing throughout the light treatment zone to provide multiple infusion ports along the length of the light treatment zone;

FIG. 14B is a cross-sectional view of the light delivery catheter of FIG. 14A proximal to the transition;

FIG. 14C is a cross-sectional view of the light delivery catheter of FIG. 14A distal to the transition;

FIG. 15A schematically illustrates a side view of a back-flush embodiment of a light delivery catheter having an infusion lumens terminating in infusion ports distal to the light delivery zone;

FIG. 15B is a cross-sectional view of the light delivery catheter of FIG. 15A proximal to the transition;

FIG. 15C is a cross-sectional view of the light delivery catheter of FIG. 15A distal to the transition;

FIG. 16A schematically illustrates a side view of a light delivery catheter with an outer shaft forming infusion lumens terminating proximal to the light treatment zone;

FIG. 16B is a cross-sectional view of the light delivery catheter of FIG. 16A proximal to the transition;

FIG. 16C is a cross-sectional view of the light delivery catheter of FIG. 16A distal to the transition;

FIG. 17A schematically illustrates the distal end of a back-flush version of a light delivery catheter having infusion lumens terminating at the distal end of the light treatment zone;

FIG. 17B is a cross-sectional view of the light delivery catheter of FIG. 17A proximal to the transition;

FIG. 17C is a cross-sectional view of the light delivery catheter of FIG. 16A distal to the transition;

FIG. 18 schematically illustrates a side view of a second embodiment of the proximal end of a light delivery catheter; and FIG. 19 schematically illustrates a side view of a third embodiment of the proximal end of a light delivery catheter.

For simplicity and clarity of illustration, the drawing figures illustrate the general elements of the light delivery catheters. Drawings of catheter assemblies are to schematically illustrate the general position of elements within the devices. Description and details of well-known features and techniques are omitted to avoid unnecessarily obscuring the invention.

DESCRIPTION

The present invention provides a light delivery catheter having an occlusion style balloon with a fluid flush, which provides superior performance over previous devices. In the treatment approach described herein, an occlusion balloon is inflated on one or both sides of the light treatment zone to block blood flow, after which a flushing fluid is infused to flush blood away from the light treatment zone. This approach can be used for application of PDT in cardiovascular indications to inhibit, stabilize and/or reduce occlusions within the cardiovascular system, including treatment of such conditions as vulnerable plaques, atherosclerosis, restenosis, intimal hyperplasia and aneurysm.

Figure 1B:
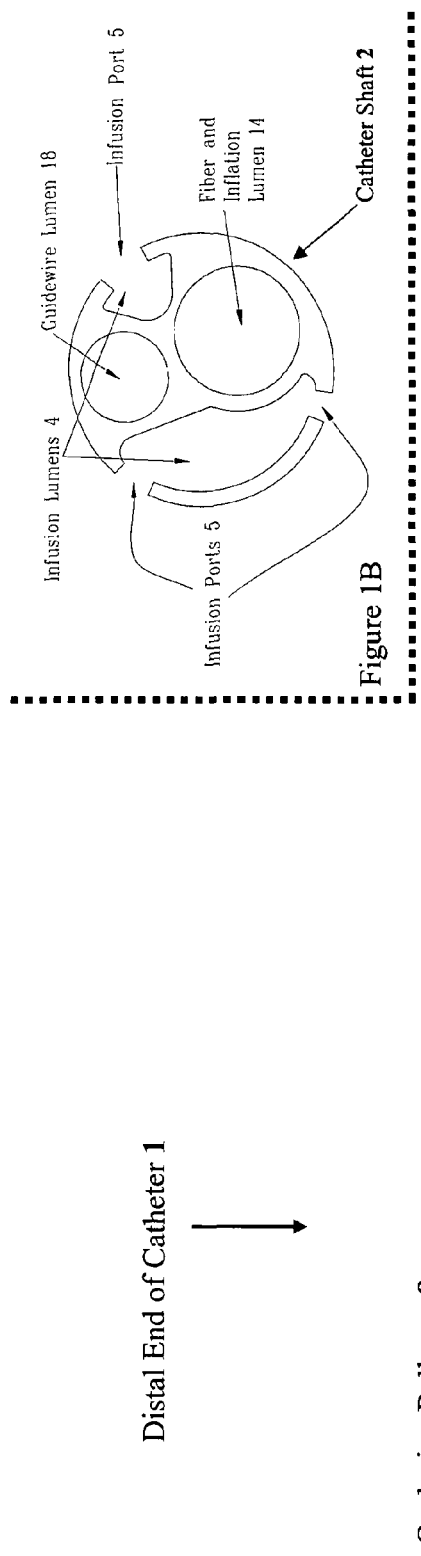
Figure 1A:
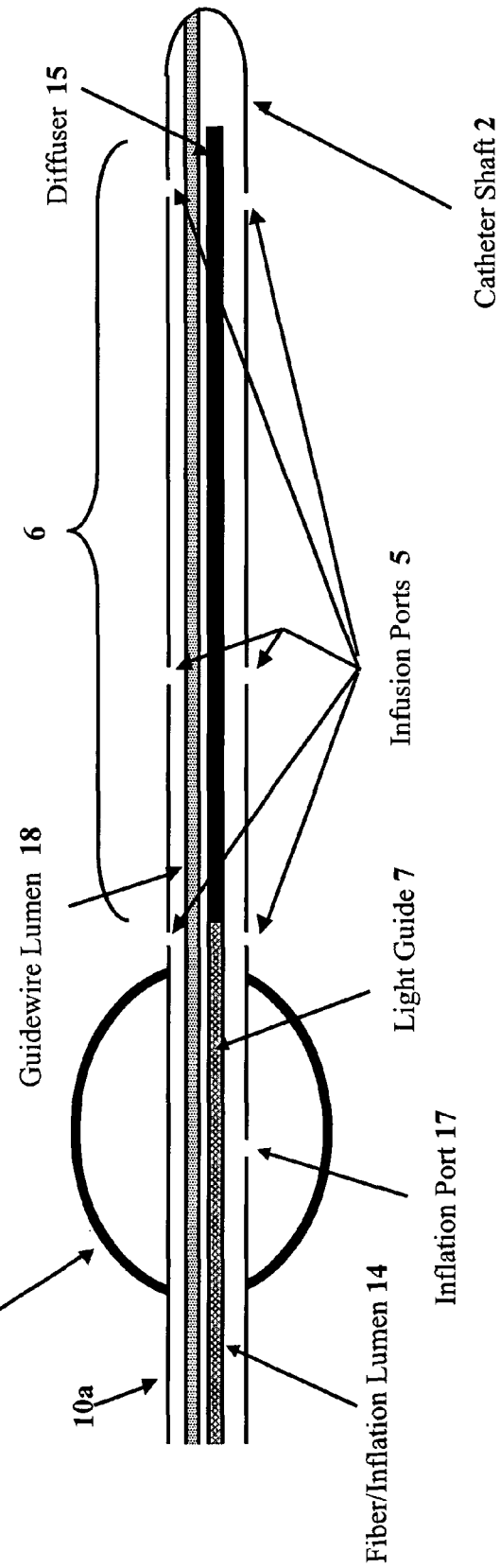

FIGS. 1A and 1B illustrate an embodiment of the distal end of an improved light delivery catheter for use in therapeutic methods, such as PDT, that require light illumination to target tissue within a blood vessel or other hollow body organ. The catheter comprises an elongated tubular catheter shaft 2 having a proximal end 3 (shown in FIG. 2) which remains outside of the body organ when in use and a distal end 1, which is inserted into the body organ when in use. The distal end 1 has a light treatment zone 6 through which light can be transmitted. The catheter shaft preferably includes a guidewire lumen 18 to allow the distal end 1 of the catheter to be advanced over a guide wire through the body organ until the light treatment zone 6 is adjacent to the target tissue. A light guide 7 in the catheter shaft 2 transmits light from a light source (not shown) at the proximal end 3 of the catheter shaft 2 to the light treatment zone 6. An occlusion balloon 8 is positioned on the distal end 1 of the catheter shaft 2 adjacent to the light treatment zone 6. An inflation lumen 14 in the catheter shaft 2 is in fluid communication with the balloon 8. Inflation lumen 14 delivers fluid from an inflation fluid source (not shown) at the proximal end 3 of the catheter shaft 2 to the balloon 8. Inflation lumen 14 can also serve as a lumen for housing light guide 7. One or more infusion lumens 4 in the catheter shaft 2 deliver infusion fluid from an infusion fluid source (not shown) at the proximal end 3 of the catheter shaft 2 to the light treatment zone 6. A plurality of infusion ports 5 are formed on the light treatment zone 6 and are in fluid communication with the infusion lumens 4. Infusion fluid is delivered to the hollow body organ through infusion ports 5, so that blood or other opaque material in the hollow body organ can be flushed from region between the light treatment zone 6 and the target tissue. Intermediate point 10a on the distal end 1 connects to intermediate point 10b at the proximal end 3 of the catheter (shown in FIG. 2).

Figure 2:
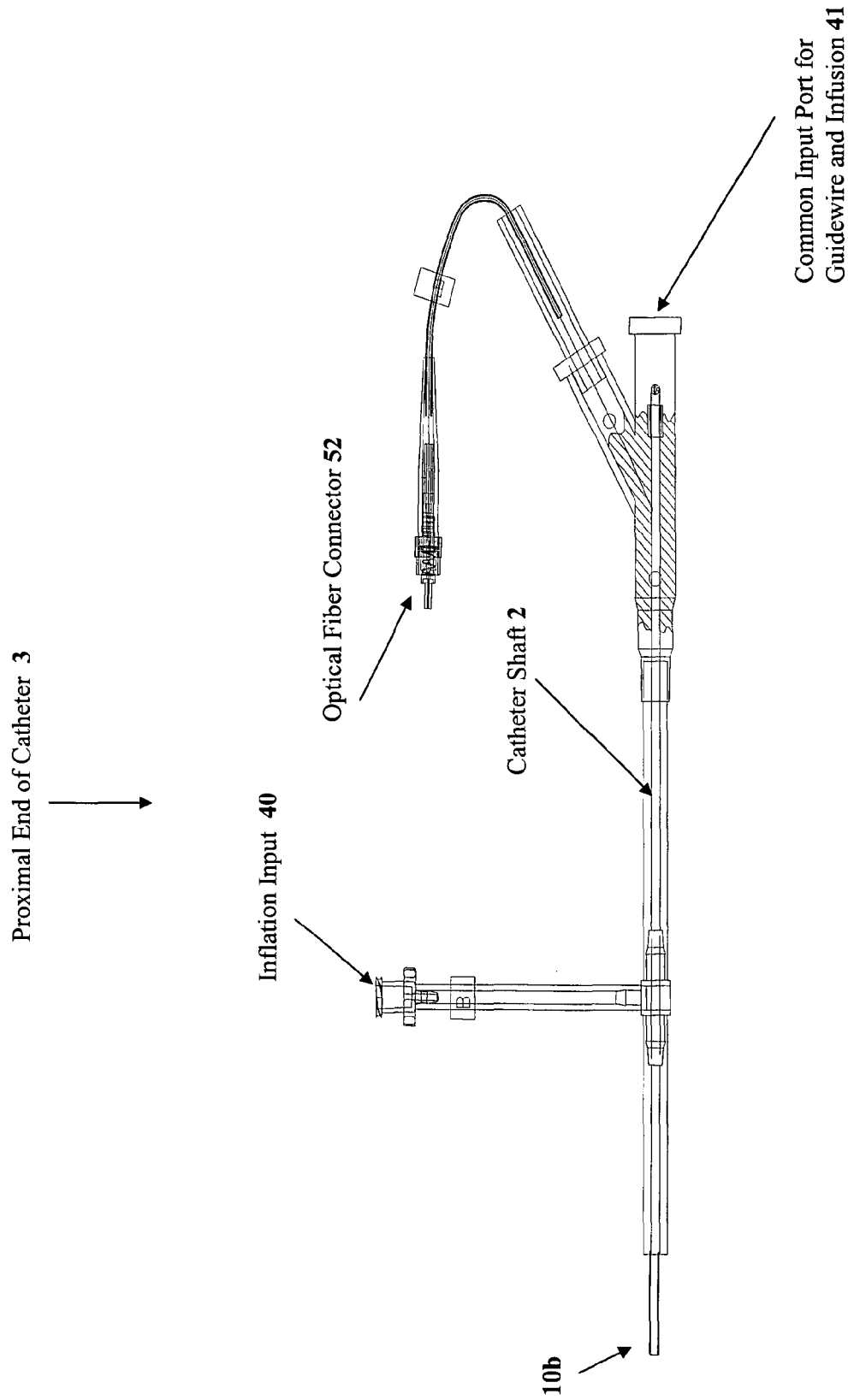

FIG. 2 illustrates an embodiment of the proximal end 3 of the catheter. When in use, the proximal end 3 remains outside of the hollow body organ. The proximal end 3 includes an inflation input port 40, which communicates with the combined fiber/inflation lumen 14 (shown in FIGS. 1A and 1B). Optical fiber connector 52 connects to a light source (not shown) to deliver light to light guide 7 (shown in FIG. 1A). A common input port for guidewire and infusion 41 communicates with the infusion lumens 4 and guidewire lumen 18 (shown in FIGS. 1A and 1B). A guidewire is inserted into guidewire lumen 18 through common input port 41. Infusion fluid is input into infusion lumen 4 through common input port 41.

Referring again to FIGS. 1A and 1B, light guide 7 is preferably an optical fiber but can be any means of transmitting light from the proximal end 3 of the catheter to the light treatment zone 6, such as an optical wave guide. The length of the light treatment zone 6 is preferably greater than 0.5 cm and includes a diffuser 15 for delivering diffuse light over an extended length. Diffuser 15 can be a modified optical fiber or a fiber tipped with a light diffusing element, which in either case are configured to emit light in a direction substantially orthogonal to the axis of catheter shaft 2. Fiber/inflation lumen 14 preferably contains an optical fiber, which is fabricated, for example, of plastic or glass. The fiber runs from the connector 52 at the proximal end 3 of the catheter shown in FIG. 2, to the distal end 1 to deliver light within the light treatment zone 6. The fiber terminates in a diffuser section 15 to allow light to be delivered along the length of the light treatment zone 6. A diffuser tip incorporating a diffusing fiber is described, for example, in Heath et al., U.S. Pat. No. 6,366, 719, and one incorporating a diffuser attached to the end of a fiber is described, for example, in Doiron et al., U.S. Pat. No. 5,269,777, both of which are incorporated by reference herein in their entirety. Alternatively, a fiber can be configured to emit light substantially from its tip in an isotropic manner. This fiber can be inserted into the fiber/inflation lumen 14 and mechanically drawn back and forth to deliver light along the length of the light treatment zone. Similarly, other light emitting elements such as LED's can be located within the light treatment zone. The device also includes means to deliver light at the proximal end 3 of the catheter, shown in FIG. 2 such that the light input at the optical fiber connector 52 exits from the light treatment zone 6 of the catheter to irradiate the desired target tissue.

The occlusion balloon 8 is preferably a compliant (elastomeric) balloon, made of a relatively low durometer material, such as latex, C-flex, polyisoprene, low durometer polyurethane, or other low durometer polymer material, with a minimal wall thickness, but can also be a non-compliant (semi-resilient) balloon. It can be located at the proximal end of the light treatment zone 6 as illustrated in FIG. 1A. Alternatively, the occlusion balloon 8 can be located at the distal end of the light treatment zone 6 as illustrated in the backflush configurations shown in FIGS. 3A, 15A, and 17A. Though the drawings show only a singe inclusion balloon by way of example, there can also be two occlusion balloons, one on either end of the light treatment zone 6.

Fiber/inflation lumen 14 runs the length of the catheter and terminates at one or more inflation ports 17 within the occlusion balloon 8 to allow it to be inflated. A means for inflating the occlusion balloon 8 can be attached to the fiber/inflation lumen 14 at the proximal end 3 of the catheter by means of inflation port 40 (shown in FIG. 2). In the illustrated embodiment, the inflation lumen and the lumen that contains the optical fiber are combined in a common lumen. In this approach, if a proximal occlusion balloon is used, a means to block fluid flow can be provided so that fluid used to inflate the occlusion balloon 8 cannot reach the diffuser section in the light treatment zone 6. This approach is advantageous when the diffuser has been designed to function in an air interface, as opposed to a liquid interface. Alternatively, separate gidewire and inflation lumens can be used.

The catheter can include a pop-off valve (not shown) at the proximal end 3 of the device, the pop-off valve being placed between the inflation port 40 shown in FIG. 2 and the actual inflation device such that it is in fluid communication with the inflation lumen 14. The pop-off valve prevents over-inflation of the occlusion balloon 8. Use of a pop-off valve is particularly advantageous when using a partially compliant occlusion balloon (e.g., polyurethane) or a non-compliant occlusion balloon (e.g., nylon). A pressure meter (not shown) can also be provided at the proximal end 3 of the device and connected to the inflation port 40 and in fluid communication with the inflation lumen 14. The pressure meter is located between the inflation port 40 and the balloon inflation device to allow the user to control inflation of the balloon 8 and to prevent over-inflation that could damage the vessel. Alternatively, occlusion balloon 8 can be inflated with a controlled volume of fluid delivered through inflation port 40 using a calibrated syringe or other suitable means.

Though not shown in the drawings, an infusion port can be located on the catheter shaft 2 adjacent and proximal to the occlusion balloon 8 to verify inflation. In this case, the infusion port has a dedicated infusion lumen. Angiographic contrast media can be infused through this port. If the balloon is inflated, the angiographic contrast media infused through this port can be seen, under angiographic visualization, to pool proximal to the occlusion balloon. If the balloon is not sufficiently inflated, the angiographic contrast media will be seen, under angiographic visualization, to flow past the occlusion balloon. If a distal occlusion balloon is being used for occlusion the extra infusion port is not necessary since the existing infusion ports can serve this same function.

Referring again to FIGS. 1A and 1B, one or more infusion lumens 4 run the length of the catheter from proximal end 3, terminating at one or more infusion ports 5 within light treatment zone 6 to allow a substantially transparent or translucent infusion fluid to be infused into the treatment site, thereby eliminating blood from the region between the light treatment zone 6 and the target tissue. The infusion flushing fluid is preferably transparent or translucent at the wavelength used in PDT. Various types of infusion fluid are acceptable, including sterile saline based solutions and electrolyte balanced solutions. Infusion fluid is injected into the infusion lumens 4 at the proximal end 3 of the catheter and exits from the infusion ports 5 at the distal end 1 of the catheter. One means for providing an infusion port is to punch a hole from the outside of the catheter shaft to access an infusion lumen. Other methods of forming infusion ports can be used as well. In some drawings only a single infusion port is shown per infusion lumen. However, multiple ports can be used in all embodiments where the infusion lumen 4 spans the light treatment zone 6 and these ports can be located along the length of the lumen so that they can span the length of the light treatment zone 6 and extend beyond it.

The use of multiple infusion ports along the length of the light treatment zone 6 minimizes the chance of semi-stagnant blood pools being trapped in the region surrounding the light treatment zone 6, thereby significantly increasing the rate and efficiency by which blood is cleared. This design also helps to eliminate blood much more quickly and efficiently than when flush is introduced at only a fixed position along the length of the catheter. This is true even when the flush rate delivered from the single fixed position is equal to the combined total flush rate from all infusion ports along the length of the catheter. This may be particularly advantageous when treating coronary arteries where occlusion times and flush volumes should be kept to a minimum.

The embodiment illustrated in FIGS. 1A and 1B comprises nine infusion ports 5 distributed longitudinally along the light treatment zone in three sets of three. Each set of three ports is positioned around the circumference of the catheter shaft at intervals of about 120 degrees of substantially uniform radial separation, such that the pressure of infusion fluid passing through the ports is generally equalized about the circumference. A similar effect can be achieved by using more or less ports radially distributed at each longitudinal position, with more or less radial separation. In a preferred embodiment, the three infusion ports closest to the occlusion balloon 8 have a diameter of approximately 0.008 inches, and the other six distal ports have a diameter of approximately 0.007 inches.

However, there are a multitude of infusion port diameters, infusion lumen diameters, pressure conditions, fluid velocities and infusion port arrangements that can achieve desired flush along the length of the light treatment zone when using such multiple port approaches. For example, the infusion ports can decrease in size with the largest holes located near the proximal end of the light treatment zone and the smallest holes located near the distal end of the light treatment zone. Alternatively, the infusion ports can increase in size along the length of the light treatment zone. The rate of infusion can also be varied along the length of the light treatment zone by varying the density of the infusion ports. The density of the ports can be increased to the point that the infusion lumen becomes essentially porous throughout the length of the light treatment zone. Alternatively, flush pressure can be varied along the length of the light treatment zone by using different lumens each having ports located at different locations along the length of the light treatment zone and with each lumen receiving different pressures. Alternatively, this same effect can be achieved by using lumens with different diameters such that the lumens provide different flow rates at the distal end of the device. In these and similar ways, the output can be modified to preferentially deliver flush fluid near the proximal end, near the distal end or uniformly along the length of the device. In the case of infusion ports being fed from a common lumen, various flow rates can be delivered from the various ports by varying the size of the opening of the ports. The particular details of how to size the holes and their location is a function of the diameter of the infusion lumen, the desired infusion pressure used, the amount of flush desired and how the flush is to be delivered, i.e., proximally loaded, distally loaded or uniform along the length of the light treatment zone. For example, when the diameter of the infusion ports is sufficiently small relative to the diameter of the infusion lumen, there can be a tendency for fluid flowing in the infusion lumen to continue along its flow path toward the distal end of the device with relatively little fluid being infused from the proximal infusion ports. However, at the distal end there may be a buildup of pressure, resulting in a higher flow rate from the most distal port, even when proximal ports are of the same diameter. Alternatively, at other pressure conditions or when the infusion port diameter is sufficiently large relative to the diameter of the infusion lumen, there is a tendency for a higher flow rate from the more proximal ports, even when all ports are of the same diameter.

For a device having a proximal occlusion balloon, with infusion delivered along the length of the light treatment zone, the first infusion port is generally located just distal to the balloon with the last port near the distal end of the light treatment zone. For devices with a distal balloon, the first infusion port is generally located near the proximal end of the light treatment zone and the last port is just proximal to the balloon. A typical spacing is 0.05 to 2 cm, although this spacing may be varied. For example, if it is desired to used a low pressure device for infusion of saline, the infusion ports that deliver this flush can be spaced closer together to decrease the total flow resistance. Alternatively, closer spacing may be used when using catheters having very small diameters designed for treating short lengths, such as in neurological applications. When using larger diameter catheters designed for treating long vessel lengths such as in femoral arteries, the hole spacing may be increased.

Additional infusion ports can be added around the periphery of the device to improve flushing. For example, two ports located on opposite sides of the catheter provide an improvement while three infusion ports located nominally at 120 degree intervals around the periphery of the catheter can provide even further improvement if the application allows a shaft diameter sufficiently large to accommodate such a number of channels. As illustrated in FIG. 1B, two infusion lumens 4 can be oriented about the periphery of the catheter shaft 2 to provide fluid to infusion ports located around the periphery of the catheter shaft but spaced at 120 degree intervals. As illustrated in FIG. 4C, three infusion lumens 4 can be oriented about the periphery of the catheter shaft 2 to provide fluid to infusion ports located around the periphery of the catheter shaft but spaced at 120° intervals. This improvement appears to be due, in part, to the tendency of the flush fluid to push the catheter away from the vessel wall, which provides a gap so that flush fluid can more efficiently flow along this gap and thereby improve the flushing efficiency.

Drugs can be delivered locally to the vessel through the catheter using one of the infusion lumens 4. For example, when delivering a photosensitizer drug for PDT, the drug can be delivered to the treatment site via an infusion lumen 4. Next saline or a similar low viscosity, essentially transparent fluid is injected via the infusion lumen 4 in order to clear any blood or drug from the treatment site. Following this step, light can be delivered to the target tissue via light treatment zone 6.

The catheter shaft 2 is preferably made of a transparent or translucent material, at least in the region of the light treatment zone 6, this material having minimal light absorption at the wavelength used in the PDT treatment. However the shaft 2 may contain a material that causes significant optical scattering. The shaft is preferably constructed of a polymer or layers of polymer and may contain a reinforcing structure such as a braid or mesh. Radiopaque marker bands (not shown) can be added to aid in positioning under angiography. The bands are preferably located at the proximal and distal ends of the diffuser 15, such that both the light treatment zone 6 and occlusion balloon 8 can be correctly positioned. A marker band can also be located on the shaft 2 within the occlusion balloon 8 or on the shaft 2 next to the occlusion balloon 8 but on the side opposite the light treatment zone 6.

FIGS. 4A, 4B and 4C illustrate various alternative lumen configurations. As illustrated in FIG. 4A, the fiber can be contained within a common fiber/inflation lumen 14 in the shaft allowing the fiber to be fully integrated into the device with the fiber lying parallel to the guidewire and with the guidewire lumen 18 extending over the entire length of the device. When using an occlusion balloon located proximal of the light treatment zone, a fluid seal (not shown) can be placed in the fiber/inflation lumen 14 between the occlusion balloon 8 and the light treatment zone 6 to prevent fluid from coming in contact with the diffuser 15.

It should be understood that the various lumens can be provided separately or combined in various configurations. As referenced herein, the term "inflation lumen" refers generally to any lumen that carries inflation fluid, even if it is also used for other purposes, such as a fiber or guidewire lumen. Likewise, the term "fiber lumen" refers generally to any lumen that can house an optical fiber or other light guide and the term "guidewire lumen" refers generally to any lumen through which a guidewire is run, even if the lumens are combined or serve another purpose. And the term "infusion lumen" refers generally to any lumen through which infusion fluid is transported, even if the lumen is combined with another lumen or serves another purpose.

Another embodiment illustrated in FIG. 4B, has a common guidewire and fiber lumen 22. The fiber is not integrated into the device in this design but rather the device is first passed over the guidewire and positioned within the body, the guidewire is then removed and the optical fiber is inserted into a guidewire/fiber lumen 22. In this case the guidewire/fiber lumen 22 runs essentially the entire length of the device. A separate inflation lumen 16 is provided.

The fiber can also be contained within its own lumen in the shaft and having a separate lumen for balloon inflation. FIG. 4C illustrates an alternative shaft cross section for an embodiment in which three infusion lumens 4 are oriented at 120 degrees around the periphery of the catheter shaft 2. This embodiment provides a separate fiber lumen 13 and inflation lumen 16.

The lumen configurations shown in FIGS. 4A, 4B and 4C are given as examples but are not intended to be an exhaustive list. For example, the fiber and infusion lumens can be combined into a single lumen. The guidewire and infusion lumens can be combined into a common lumen. Alternatively, the fiber, guidewire and infusion lumens can be combined into a single lumen. In the case of the infusion lumens, multiple lumens can be used that are oriented around the periphery of the catheter shaft. Alternatively, these separate lumens can be connected such that they are in fluid communication with each other along the entire length of the device.

Figure 5B:
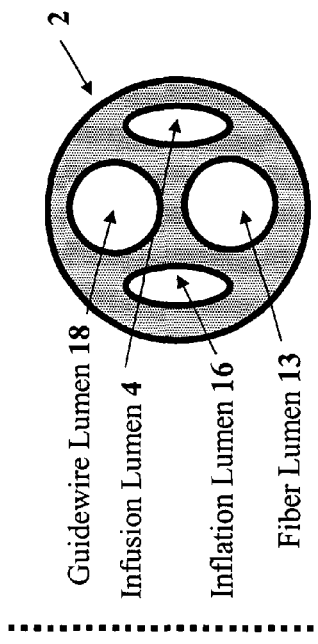
Figure 5A:
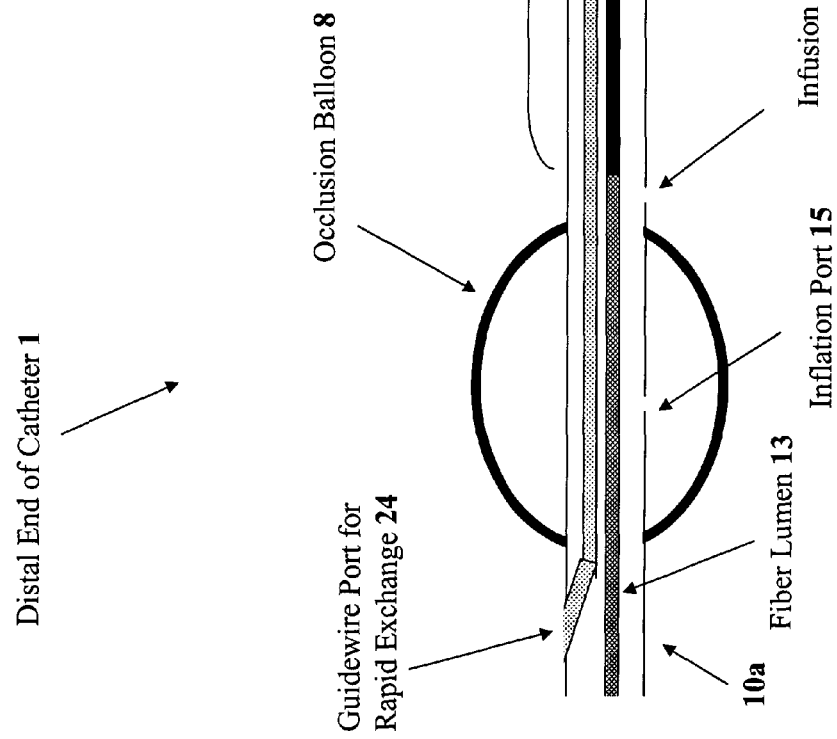
Figure 6B:
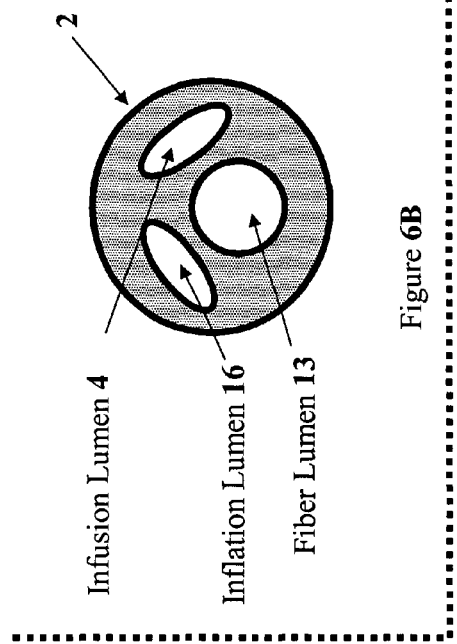
Figure 6A:
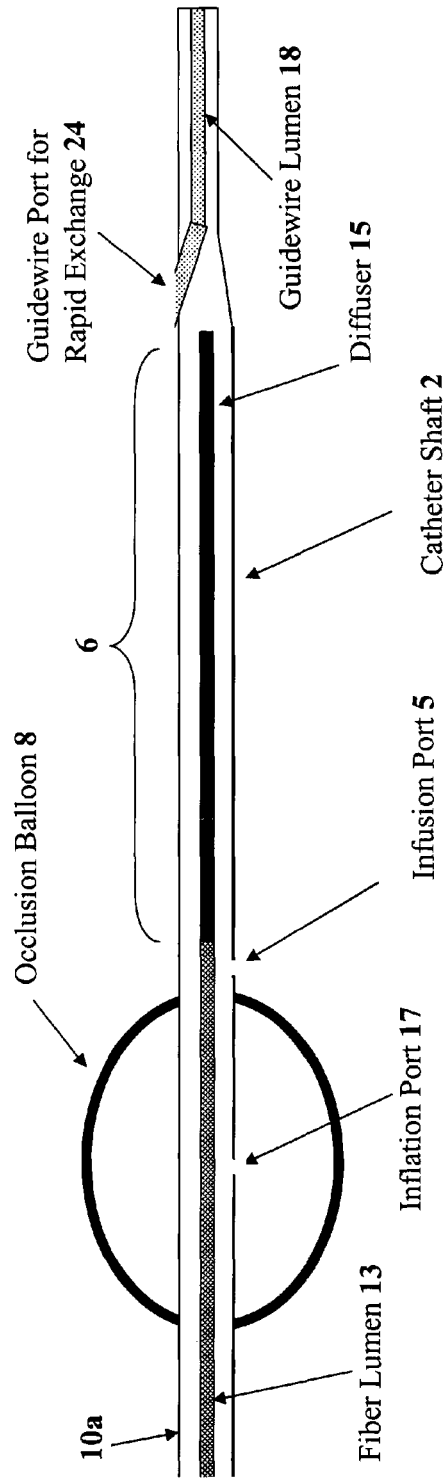

The guidewire lumen can be designed to accommodate a rapid exchange mode. A typical example is illustrated in FIGS. 5A and 5B using a single proximal occlusion balloon. The guidewire lumen 18 originates at a rapid exchange guidewire port 24 proximal to the light treatment zone 6 and occlusion balloon 8. As illustrated in FIGS. 6A and 6B, a rapid exchange port 24 can also be located distal of the light treatment zone and with a single occlusion balloon 8 proximal to the light treatment zone 6.

Any of the embodiments described herein can include one or more centering balloons located approximately within the light treatment zone 6. An example of a light delivery catheter including a centering balloon is illustrated in FIGS. 7A and 7B. The centering balloon 25 is preferably made of a non-compliant material such as nylon, PET or high durometer polyurethane, such that it has a well-defined diameter when inflated. The centering balloon is inflated through inflation lumen 16 and inflation port 27. In this embodiment, the centering balloon 25 is connected to an inflation lumen 16 that is common with the occlusion balloon 8. Alternatively, the centering balloon and occlusion balloon can be inflated using separate inflation lumens. The centering balloon 25 preferably has a diameter that is slightly less than the vessel diameter. When inflated, the centering balloon 25 holds the catheter shaft 2 away from the vessel wall to improve light dose uniformity. It is preferably made of a sufficiently non-compliant material such that its inflated diameter is restricted to prevent it from causing significant injury to the vessel. Preferably, the inflated diameter and inflated pressure are such that a saline infusion fluid can flow past the centering balloon 25.

Figure 8B:
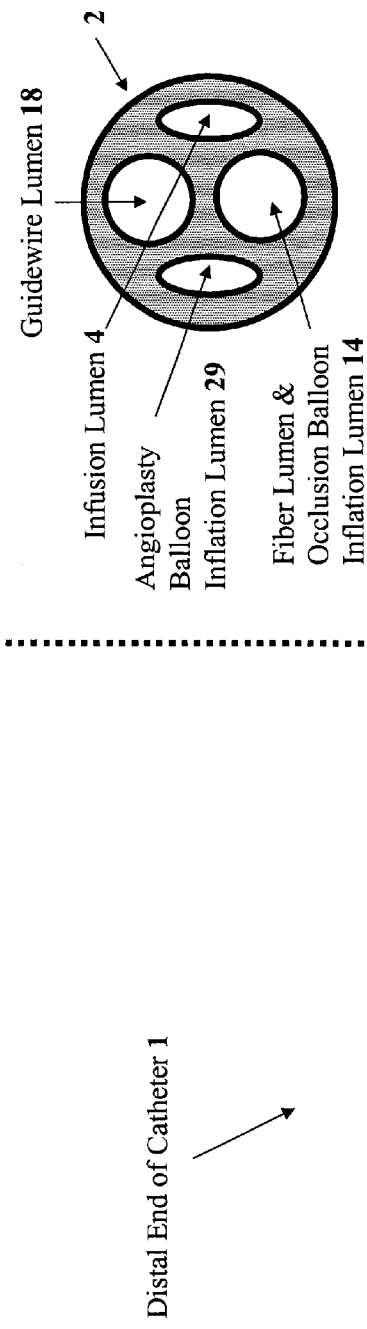
Figure 8A:
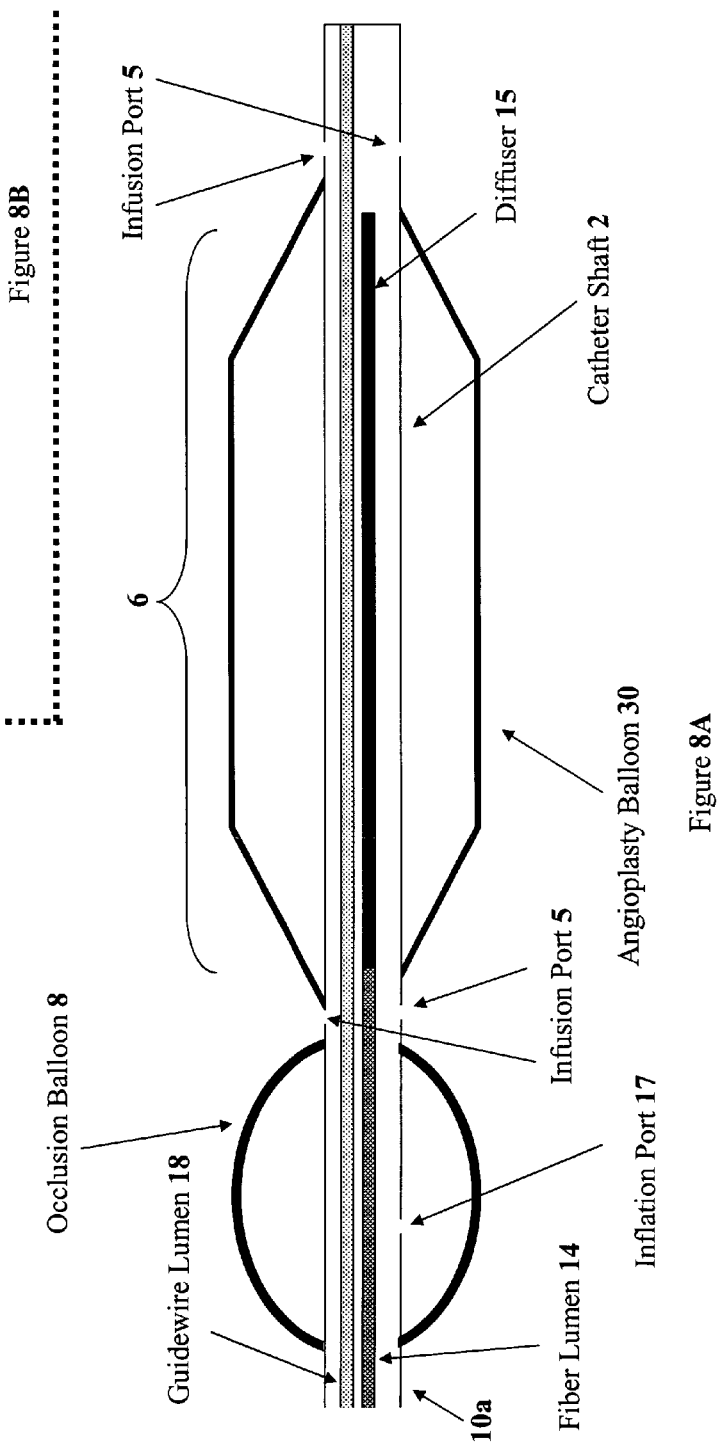

In another embodiment illustrated in FIGS. 8A and 8B, a non-compliant angioplasty balloon 30 is positioned over light treatment zone 6. The angioplasty balloon 30 allows the device to be used as an angioplasty device to mechanically open the vessel and/or deliver a stent. When an angioplasty balloon is used, another inflation lumen 29 dedicated to the angioplasty balloon 30 is preferably added to accommodate the high pressures that are generally used in such balloons. The example shown in FIGS. 8A and 8B provides a means for drug delivery (via the infusion lumen 4), angioplasty and light delivery. When used to deliver drugs that are not readily taken up within the target tissue, both proximal and distal occlusion balloons can be used to trap the drug between the balloons and thereby increase their contact time with the vessel wall to improve the efficiency of drug delivery. When an angioplasty balloon is used in this manner, infusion ports can be located both proximal and distal to the angioplasty balloon.

As illustrated in FIGS. 9A and 9B, the guidewire lumen 18 can function as a perfusion channel. Perfusion ports 32 are created proximal to the light treatment zone 6 and proximal to any occlusion or light treatment balloons. The perfusion ports 32 allow a limited amount of blood to flow from outside the catheter into the guidewire lumen 18. When the guidewire is retracted, blood enters the perfusion ports 32 and flows down the guidewire lumen 18 and exits out the distal end of the device. In this way, blood can flow past the occlusion balloon 8 and light treatment zone 6 even when the occlusion balloon 8 is inflated. However, the blood is confined within the catheter shaft 2 such that light absorption by the blood is minimal.

Figures 10A, 10B:
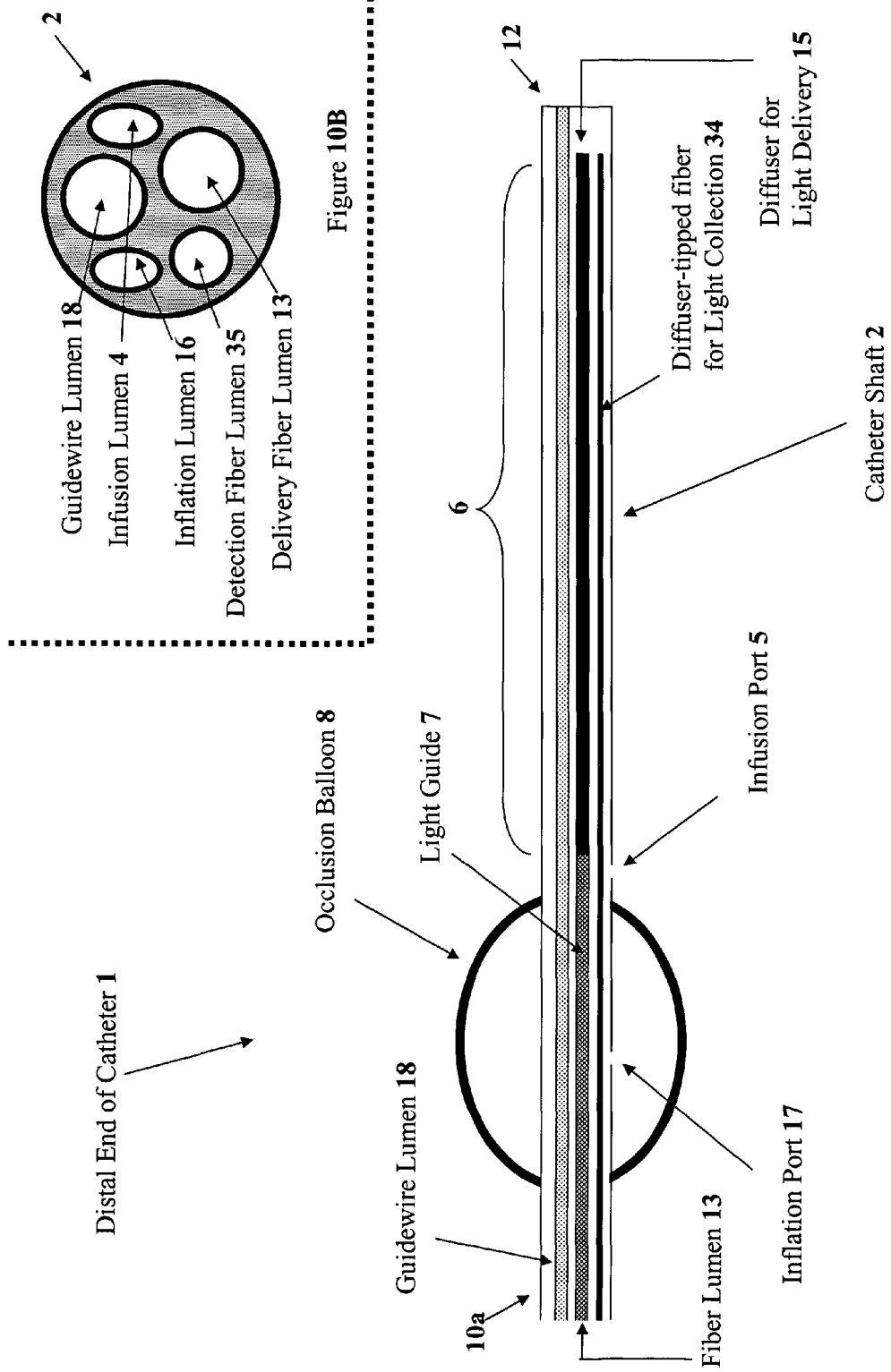

FIGS. 10A and 10B illustrate another embodiment of the light delivery catheter, which includes a light detection fiber 34. This light detection fiber 34 is constructed with scattering material at its distal end, which allows light that is emitted from the diffuser 15 to enter the second light detection fiber 34. This light propagates within this light detection fiber 34 positioned within detection fiber lumen 35 from the distal end 1 of the catheter back to its proximal end 3. Monitoring means (not shown) are provided at the proximal end of the light detection fiber 34, which allow its optical output power to be measured, thereby providing a means of monitoring the power that is being delivered at the distal end 1 of the device. This monitor can be calibrated before the catheter is inserted into the body to provide a calibrated means of monitoring output power.

A small amount of fluorescent material can be incorporated at the distal end of this second light detection fiber 34. The emission characteristics of this fluorescent material are such that when it is irradiated with the wavelength used for the PDT treatment, it emits fluorescence at a different wavelength. This fluorescent material can be made of an inorganic ground crystalline material that absorbs one wavelength and emits a second wavelength which is typically longer than the incident wavelength. An inorganic may be used since such materials tend to be more stable and less likely to photobleach. This fluorescent emission can be detected at the proximal end of the light detection fiber 34, thereby providing a means of monitoring optical dose being delivered to the treatment site. The detection means can include a narrowband filter to pass the fluorescent wavelength and reject extraneous wavelengths, particularly the wavelength used for PDT excitation.

The fluorescent material can also be incorporated at the distal end of the diffuser 15. This embodiment can be used to provide detection without the second detection fiber 34. Light that reaches the distal end of the diffuser 15 generates fluorescence, some of which propagates back to the proximal end of the fiber 7. This fluorescence, being of a different wavelength than the PDT treatment light, can be separated using a dichroic beam splitter or similar wavelength selective optical element. Once separated from the PDT treatment wavelength, the fluorescence can be detected and used to monitor the delivered power in a manner similar to that described above.

Another aspect of the invention provides improved infusion lumens for use with light delivery catheters. For treatment of small vessels in which the distal end of the catheter must have a low cross sectional area, a smaller diameter catheter shaft with smaller diameter infusion lumens is preferable. However, small diameter infusion lumens can make it difficult to deliver sufficient pressure at the distal end of the catheter to provide adequate flush. This can be overcome by using a catheter shaft design that has larger diameter infusion lumens near its proximal end and smaller diameter lumens near its distal end. The larger diameter infusion lumens in the proximal region allow a higher pressure to be provided at the distal end of the catheter to maintain the flow of the infused flushing fluid at the distal end. One embodiment of this concept is illustrated in FIG. 11A. As shown in that figure, the cross section of the infusion lumens is relatively large at the proximal end of the catheter with those lumens tapering down to a smaller diameter in a region proximal of the light treatment zone. The particular point at which this transition occurs is not critical, as long as the infusion lumens have the larger diameter along the majority of the length of the catheter. While FIG. 11A shows the lumens with a gradual taper, the desired outcome can also be achieved by using a proximal shaft having larger diameter infusion lumens and a distal shaft having smaller diameter infusion lumens and butt welding these two shafts together at a point proximal of the light treatment zone.

As shown in FIGS. 11A, 11B and 11C, the catheter shaft 2 is provided with a variable diameter which forms a narrowing transition 39 proximal to the light treatment zone 6. The narrowing transition 39 reduces the diameter of the catheter shaft 2 and the diameter of the infusion lumens proximal to the light treatment zone 6, allowing the distal end to be easily inserted into a narrow vessel. The catheter shaft 2 comprises one or more infusion lumens 4 having a variable diameter. The diameter of the infusion lumens 4 decreases at the transition 39 of the catheter shaft 2, such that the infusion lumens have a constricted portion along the light treatment zone. Such a configuration allows desired infusion flow rates to be achieved while maintaining relatively low pressures, even when the distal tip of the device is relatively small. As used herein, the term "narrowing transition" refers generally to any means of reducing the diameter of the catheter shaft, such as by tapering the shaft or more abruptly reducing the diameter, e.g., by connecting (e.g., butt welding) a shaft having larger diameter to one having a smaller diameter. By increasing the diameter of the infusion lumen in that part of the vessel that will accommodate a larger diameter shaft, there is a decreased resistance to fluid flow than would be the case if a fixed diameter infusion lumen (equal in diameter to that used at the distal tip of the device) were used along the entire length of the device. Such a configuration allows desired flow rates to be achieved while maintaining relatively low pressures, even when the diameter of the distal infusion lumen is small.

An alternative means of providing high flush rates while maintaining a low cross section in the light treatment zone is illustrated in FIGS. 12A, 12B and 12C. Here, the device has a larger diameter shaft proximal to the light treatment zone 6 and a smaller diameter shaft in the region of the light treatment zone 6 to allow the distal end of the device, which contains the diffuser 15, to be inserted into smaller diameter vessels. In the illustrated embodiment, the shaft reduces diameter at transition 39, which separates the distal end of the shaft into a proximal portion 2a and a distal portion 2b. Six lumens pass through the proximal portion 2a, with four of the six continuing through light treatment zone 6 via distal portion 2b. The continuing lumens distal to the transition 39 are a fiber lumen 14, infusion lumens 4b, and guidewire lumen 18. Where the reduction of six lumens to four lumens occurs, the two lumens that terminate are infusion lumens 4a. These two infusion lumens 4a terminate at infusion ports 5a and 5b, such that the flush stream originating from these ports is directed distally towards the light treatment zone 6. Infusion ports 5c and 5d can also be provided to direct flush fluid sideways toward the vessel wall. If very small vessels are to be treated, the shaft diameter can be reduced further by using a common guidewire and fiber lumen in both the proximal catheter shaft 2a and the distal catheter shaft 2b, or by eliminating the infusion lumens 4b. Alternatively, to accommodate the requirements that infusion lumens 4b have small diameters, these infusion lumens can have a significantly larger diameter at the proximal end of the catheter and transition down to a smaller diameter proximal of the occlusion balloon as described in connection with FIGS. 11A, 11B and 11C.

FIGS. 13A, 13B and 13C illustrate an embodiment in which a single infusion lumen 4 terminates just proximal to the light treatment zone 6. Infusion lumen 4 may have one or more infusion ports. Infusion ports may be directed in the forward direction, sideways direction or both. In the illustrated embodiment, infusion port 5a is directed in the forward direction and infusion port 5c is directed in the sideways direction toward the vessel wall.

FIGS. 14A, 14B and 14C illustrate an embodiment of the catheter having two infusion lumens, wherein one infusion lumen terminates proximal to the light treatment zone while the other continues to the distal end of the light treatment zone to provide multiple infusion ports along the length of the light treatment zone. Infusion lumen 4a terminates at the proximal end of the light treatment zone 6 and the infusion lumen 4b terminates at the distal end of the light treatment zone 6. Lumen 4b has multiple infusion ports 5 located throughout the length of the light treatment zone 6.

FIGS. 15A, 15B and 15C illustrate an embodiment where the distal end of the catheter shaft is reduced in diameter, similar to that described in the previous figures, except here the occlusion balloon 8 is located on the distal end and the infusion lumens 4 terminate near the distal end of the light treatment zone 6. This embodiment incorporates infusion lumens 4 having multiple ports 5 located along the length of the light treatment zone 6 with the distal end of the lumens 4 open to allow fluid to be delivered from the end of these lumens. As can be seen from examining the other figures, multiple combinations can be used here, examples of which are: distal end of lumens sealed with multiple ports throughout light treatment zone, no ports throughout the light treatment zone with only the distal ends of lumens open to provide flush ports, multiple flush ports alternately spaced on the different lumens throughout the light treatment zone, only a single infusion lumen instead of two, etc. Also, in this embodiment and several previous illustrations, the fiber lumen and inflation lumen are combined to utilize a common lumen. Alternatively, in this and previously illustrated embodiments, separate lumens could also be used for the fiber and inflation of the occlusion balloon. Similarly, one or multiple infusion lumens can be used, although it is preferable to use at least two lumens in this design to ensure that flush is directed somewhat symmetrically around the catheter shaft. Similarly, the infusion lumens may have diameters that are larger at the proximal end of the catheter than at the distal end to allow higher pressures and associated higher infusion rates to be delivered at infusion ports 5, as described in conjunction with FIGS. 11A, 11B and 11C.

As illustrated in FIGS. 16A, 16B, and 16C, the catheter can also be constructed as a shaft within a shaft. In this embodiment the inner shaft 2b is comprised of the guidewire lumen 18 and fiber lumen 13. The inner shaft 2b is contained within the infusion lumen 4 of the outer shaft 2a. The outer shaft 2a also houses an infusion lumen 4 and the inflation lumen 16. At the proximal end of the catheter 3 (shown in FIG. 2), the inner shaft 2b extends proximal to the outer shaft to allow the guidewire and fiber to be easily inserted. The inner shaft 2b also protrudes from the distal end of the infusion lumen 4 by a distance that is at least as long as the diffuser 15. The occlusion balloon 8 is mounted on the distal end of the outer shaft 2a and is inflated and deflated via the inflation lumen 16 and inflation port 17. At the distal end, the outer shaft and associated infusion lumen 4 terminate just proximal to the diffuser 15. The infusion lumen 4 provides a conduit for flushing media to be directed towards and around the circumference of the fiber diffuser 15 in order to clear blood from the light treatment zone 6. Similarly, drugs can be locally delivered using this approach. To maintain flush output around the circumference of the fiber diffuser 15 and to prevent the inner and outer shafts from moving relative to each other, the two shafts can be mechanically connected near the distal end of the outer shaft 2a. This mechanical connection is preferably made in a manner that helps to center the inner shaft 2b within the outer shaft 2a, but so as to not substantially block fluid flow. The mechanical connection is generally located within three centimeters of the distal end of the outer shaft 2a. Various means such as epoxy, heat bonds or mechanical ribs can be used to form the connection.

A similar embodiment using coaxial shafts is shown in FIGS. 17A, 17B, and 17C. The coaxial shafts used here are similar to those used in FIGS. 16A-C, except now the outer shaft 2a continues to the distal end of the light treatment zone 6 where it is connected to the inner shaft 2b as described above. The occlusion balloon 8 is positioned distal to the light treatment zone 6 and is inflated either with a dedicated infusion lumen (not shown) or with a common fiber/inflation lumen 14 as shown in FIG. 17A. Infusion ports 5 can be located such that infusion fluid flows from at the distal end of the outer shaft in the forward direction, from the distal end of the outer shaft but directed sideways toward the vessel wall, or from multiple ports located along the length of the light treatment zone. For illustration purposes, all of these possibilities are shown in FIG. 17A. This design is advantageous when delivering the light near the proximal end of a larger diameter vessel.

FIG. 18 illustrates an alternative embodiment of the proximal end of the catheter. Intermediate point 10b connects to intermediate point 10a on distal end 1 (shown in previous figures). Inflation port 40 connects to the inflation lumen. Infusion input 42 connects to the infusion lumen. Optical fiber connector 52 connects the light guide to a light source. A guidewire is inserted into guidewire lumen 18 through guidewire input port 46.

FIG. 19 illustrates another embodiment of the proximal end of the catheter. Inflation port 40 connects to the inflation lumen. Infusion input 42 connects to the infusion lumen. Optical fiber connector 52 connects the light guide to a light source. A guidewire is inserted into guidewire lumen 18 through guidewire input port 46. All input ports connect to the shaft via common port 54.

The occlusion/infusion catheters described here can be used in a variety of ways. For example, since the flow rate of the flush is relatively low, the flush can be initiated prior to inserting the catheter into the body and can be left on for the entire procedure. With this approach the operator is only responsible for inflating and deflating the occlusion balloon. Alternatively, the flush can be used only when the device is positioned or only when the occlusion balloon is inflated. One or more boluses of flush fluid can be infused immediately after inflation of the occlusion balloon. This tends to quickly clear the blood from the light treatment zone, thereby maximizing the amount of light that can be delivered to the vessel wall in a given period of time. Since the occlusion balloon blocks blood flow, there is a minimal amount of blood entering the light treatment field from the proximal (as defined by the nominal direction of blood flow) side of the vessel. Furthermore, because the back-pressure from the venous side is relatively low, there is minimal blood entering from the distal region of the vessel. However, in practice it may be beneficial to provide a continuous low pressure flush throughout the period of the light treatment. This maintains a positive pressure in the vessel within the light treatment field, thereby helping to prevent blood from flowing back into the light treatment field. Furthermore, continuous flow helps to sweep away any small amounts of blood that may enter the light treatment zone via leakage around the occlusion balloon or by similar means. Of course, there are a multitude of similar methods by which the flush fluid can be delivered, similar to those described above.

The unexpected improvement in treatment outcome that can be obtained using the devices and methods described above, relative to previous approaches, results in part from better elimination of blood with reduced risk of mechanical trauma to the vessel. While the benefit of improved blood elimination is most pronounced at shorter wavelengths where light attenuation by blood is most significant, it exists for longer wavelengths as well since blood also significantly attenuates light throughout the visible and infrared portions of the spectrum.

One reason why the improved outcome achieved by the devices and methods described herein was unexpected is the perception concerning the importance of centering the source within the vessel. One of the purported advantages of the angioplasty balloon approach is the ability of that approach to center the light source within the vessel. However, the biological response when using the occlusion/infusion design displays good circumferential uniformity regardless of how well the source is centered. However, this circumferential uniformity is only present when blood is efficiently eliminated from the light treatment zone. Based on these characteristics, the circumferential uniformity seen with the occlusion/infusion design is likely due to the combination of the light scattering characteristics of tissue and the efficient elimination of blood. Since tissue tends to strongly scatter light, placing a light source within a vessel is analogous to placing it within an optical integrating sphere. For example, if the light source is off-center, it will deliver a higher irradiance to the vessel wall which lies nearest to it, with the lowest irradiance being delivered to the vessel wall that lies farthest away. However, the scattering properties of the tissue will cause much of the light from the nearest wall to be scattered to the farthest and vice versa. The net result is a significantly more homogeneous distribution of light within the vessel wall when the source is off-center than might otherwise be expected. However, this effect is only achieved if blood is efficiently eliminated from the light treatment zone, since this blood would otherwise tend to absorb the light before it could scatter sufficiently to achieve a homogeneous light distribution. As a result, the occlusion/infusion design approach delivers a more uniform light dose than would be achieved with bare fiber approaches used previously since these do not provide the means to eliminate blood. While this light homogenizing effect of tissue will not provide the same degree of uniformity as would be obtained from a perfectly centered light source, the biological result obtained by such a non-centered source is insignificant, contrary to what has been described in the prior art.

In addition to the biological results described above, the catheters described herein provide the additional advantage of allowing the user to leave the guidewire in place during light delivery. Previous designs have either attempted to use concentric diffusers and guidewires, or have relied on the user removing the guidewire prior to light treatment. By efficiently eliminating blood and thereby allowing significant light scattering without significant absorption of light by blood, the need to either remove the guidewire or use a concentric diffuser and guidewire can be avoided. This simplifies the device design and results in a safer clinical procedure.

Another benefit of the occlusion/infusion design over the angioplasty balloon design results from the materials used in balloon fabrication. The occlusion/infusion approach avoids the inflation problems associated with the combination of a balloon having a long length and non-compliant balloon shape. In practice it is difficult to fabricate practical compliant balloons having lengths that are much larger than their diameters since such balloons have a tendency to not inflate uniformly over a long length. (Even if such a balloon could be fabricated it would still trap a thin layer of blood between the balloon and the vessel wall, particularly in vessels containing stents or other complex morphologies.) With the occlusion/infusion approach, a balloon having a short length is inflated either proximal or distal to the light treatment zone. Since the only requirement is for the inflated balloon to block blood flow, this balloon can have a very short length as opposed to the angioplasty balloon approach. Furthermore, it is not necessary that this occlusion balloon inflate uniformly since the need to have the light source centered within the vessel is eliminated. Consequently, a compliant (more elastic) material can be used to fabricate the balloon, which prevents minimal risk of mechanical damage even when the balloon is over-inflated. This benefit is a result of the compliant nature of elastic balloon materials.

A further benefit of using a compliant occlusion balloon is reduced risk of mechanical damage if the balloon is inadvertently over-inflated. If such over-inflation occurs with a compliant balloon it tends to expand along the length of the vessel, rather than outward. However, a non-compliant balloon would tend to expand outward, thereby risking mechanical damage to the vessel.

However, a non-elastic balloon can also be used with the catheters disclosed herein as long as it is properly sized to the vessel and over-inflation is avoided. In either case it is important to note that the purpose of the balloon used in the occlusion/infusion catheter is simply to block or significantly reduce blood flow, unlike the angioplasty balloon design where the balloon must eliminate blood by displacing it. A significant risk associated with non-elastic balloons—the tendency to cause mechanical vessel damage when inflated over a long length in tortuous or tapering vessels—can be avoided since an occlusion balloon can be of a short length and low pressure.

The integrated diffuser tipped fiber also provides significant advantages over prior fiber optic devices that emit light at essentially a single point. Use of a fiber that emits light at a single point requires that the operator mechanically slide the fiber relative to the catheter in order to achieve light treatment along a length of vessel. The need for such manual operation is eliminated by inclusion of a diffuser as described herein. Furthermore, by integrating the fiber into the catheter in a fixed manner, as described in some of the designs disclosed here, the operator can position a single fully integrated catheter and does not have the burden of separately positioning the catheter and the light delivery fiber. Finally, this integrated approach allows the use of more flexible fibers since there is no need for requirement for fiber to be stiff enough that the operator can insert it to the distal end of the catheter. This results in a catheter that is more flexible overall, and, consequently, better able to access more distal blood vessels.

In addition to the unexpected performance cited above, the catheter design and methods described herein provide additional advantages over previous approaches. As described above, when using the angioplasty balloon approach, the balloon can cause mechanical trauma to the vessel wall along the length of the inflated angioplasty balloon, due to the non-compliant nature of the balloon as described above. The resulting injury response can result in undesirable outcomes, such as development of intimal hyperplasia, which causes restenosis. Since cardiovascular PDT is designed to inhibit such injury responses, this is not a significant drawback as long as a sufficiently high light dose is delivered to the vessel wall. Unfortunately, such a sufficient light dose cannot be delivered at the ends of the balloon since the light can only be delivered over the length of the diffuser but not at the ends of the balloon where blood is present. This prevents an adequate light dose from being delivered at the ends of the balloon and would be expected to result in the edge effects seen with other cardiovascular treatments, including drug-coated stents and brachytherapy. Since the occlusion/infusion design eliminates blood from either end of the light source and, more importantly, does not induce mechanical trauma within the region of the light treatment zone, the likelihood of such edge effects is significantly reduced. While the occlusion balloon inflated at either end of the light treatment zone could potentially induce mechanical trauma, this is highly unlikely with properly designed compliant balloons. Furthermore, this is also unlikely when using a non-compliant occlusion balloon as described here as long as the balloon is properly sized. The reason for such a reduced risk of damage from a non-compliant occlusion balloon is that since it is very short it does not have the drawbacks associated with inflation over a long length in tortuous or tapering vessels as described above for conventional angioplasty balloon designs. Other promising applications include the treatment of atherosclerosis by causing the size of the plaque to regress and stabilization of vulnerable plaque and aneurysm through elimination of inflammation. In all these cases it is highly desired that the target treatment site not undergo mechanical trauma since such trauma could exacerbate the existing disease. The occlusion/infusion approach used here achieves that goal since, unlike previous approaches, this approach avoids mechanical contact with the target treatment site.

Another advantage of the devices and methods described herein is reduced mechanical trauma within the light treatment field. One of the applications of PDT is the treatment of angioplasty sites within a vessel to inhibit a restenotic injury response. However, to achieve an appropriate biological inhibition response with PDT it is necessary to deliver the PDT treatment beyond either end of the angioplasty zone. When using a modified angioplasty balloon to displace blood and deliver light, a longer balloon is required for light delivery than is used for the balloon angioplasty in order to effectively deliver light beyond either side of the angioplasty region. Use of such a longer balloon also minimizes the risk of misalignment between the angioplasty treatment site and the delivered light dose. However, use of such an angioplasty style light delivery balloon that is longer than the angioplasty balloon risks introducing additional trauma to the vessel wall, particularly in those regions of the vessel beyond the site of the angioplasty. Such a result, wherein the treatment therapy intended to prevent an injury response actually induces an injury response, is clearly unacceptable.

Another advantage of this approach is improved ability to treat long tortuous vessels. When using a light-emitting element within a modified angioplasty balloon it is necessary to fully inflate the balloon to adequately displace blood to allow adequate light delivery. However, this can be difficult in tortuous vessels, especially if the treatment length is greater than 1-2 cm. This is due to the fact that, when inflated, the non-compliant, modified angioplasty balloon tends to inflate in a straight line, rather than follow the curvature of tortuous vessels. The result is that the balloon tends to straighten the vessel, resulting in undesired mechanical trauma to the vessel. This limitation cannot be overcome by under-inflation of the angioplasty style light delivery balloon since under inflation results in inadequate displacement of blood. The only effective solution to this problem is to use a short balloon (1-2 cm in length) and deliver the treatment in a stepwise manner, treating short sections of vessel with each step.

Another advantage of the catheter of the present invention is the ability to treat small diameter vessels. When using the modified angioplasty balloon approach, it is necessary to mount the non-compliant angioplasty balloon on the catheter shaft overlapping the light treatment zone. However, use of such a non-compliant balloon adds to the overall device profile, thereby limiting access to small vessel diameters. Furthermore, the vessel diameter must be sufficiently large to allow for inflation of the balloon along its length. With the occlusion/infusion approach disclosed the balloon is mounted away from the light treatment zone, generally well proximal to the light treatment zone. Consequently, since there is no need to locate a balloon at the distal end of the device, the ultimate diameter of the occlusion/infusion device can be smaller allowing treatment of smaller vessels.

Another advantage of the occlusion/infusion device is in the treatment of vessels whose diameter tapers or otherwise changes within the length of the section to be treated. When using a modified angioplasty style balloon it is necessary to inflate the balloon to displace the blood, which can lead to induction of significant injury within the smaller diameter regions of the vessel being treated. Since the occlusion/infusion device does not require inflation of such a balloon, this problem is avoided altogether. Furthermore, the occlusion balloon that is inflated on the occlusion/infusion device is either compliant or, even if non-compliant, is of a short length, typically on the order of 5 mm. Therefore, there is no similar limitation associated with inflation of the occlusion balloon outside the light treatment zone.

Another advantage of the devices described herein is their ability to treat multiple vessel diameters with a single device. With the modified angioplasty balloon approach the device must be correctly sized to the vessel to be treated. This requires that a significant stock of devices be kept on hand and also limits the various vessel geometries that can be treated. However, these limitations can be completely avoided with the occlusion/infusion style light delivery device using a compliant balloon since the compliant balloon allows a wide range of vessel diameters to be treated with a single device. Similarly, a single device can be used on a patient at multiple locations within the cardiovascular system unlike what would be the case with an angioplasty balloon approach.

Another advantage of the devices describe herein is the integration of multiple features. As described above, one or more occlusion balloons can be located on the catheter shaft, well outside the desired light treatment zone. Since these balloons are located well away from the light treatment zone, this allows other features to be mounted on that part of the catheter shaft overlapping the light treatment zone, as described in U.S. application Ser. No. 10/634,665, entitled Catheter and Method for Diagnosis and Treatment of Diseased Vessels, filed concurrently herewith and incorporated herein by reference in its entirety. Features that can be incorporated within this portion of the catheter shaft include a separate angioplasty style balloon, means for local drug delivery, means to detect disease, etc.

In addition to the design improvements highlighted above, the light delivery catheter of the present invention can use multiple infusion ports to further overcome the shortcomings of prior light delivery catheter designs. When attempting to displace blood from a straight section of vessel using conventional flushing mechanisms, there can be a tendency for the fluid delivered from a given infusion port to preferentially follow a particular flow path. While this can provide effective blood elimination along that particular flow path, pockets of residual blood lying outside the primary flow path can remain. These blood pockets can compromise the efficacy of the treatment due to absorption of light. An even more significant problem arises when attempting to treat a vessel segment that includes a branch vessel, as is often the case in practice. In the case of such a branch, the flush fluid tends to flow along the length of the device until it reaches the branch, at which point the majority of the flush fluid flows down the branch. This results in inadequate flushing of the vessel segment beyond the branch point. This tendency of the fluid to flow down the branch vessel, rather than the intended vessel, is a result of the fact that the light delivery catheter can occupy a significant portion of the main vessel in which it is located. In this way the catheter can act to provide higher flow resistance in the main vessel than in the branch, hence a significant portion of the flush fluid passes down the lower resistance branch vessel leaving the main vessel, which is the target of the treatment, with insufficient flush to adequately clear the blood.

An effective means for overcoming both of these limitations is to locate multiple infusion ports along the length of the catheter within the light treatment zone. This design can provide a significant benefit over a design in which flush is delivered at a fixed location along the length of the catheter. First of all, when fluid is emitted from multiple infusion ports along the length of the catheter, the previously described tendency for trapping of residual pockets of blood within the light treatment zone is significantly reduced. This leads to less attenuation of light by blood and a much more uniform and efficacious biological response. This benefit is particularly significant when using short wavelengths of light, particularly those for which absorption of light by blood is high. The additional infusion ports most likely increase flow turbulence, which appears to help dislodge pockets of blood. It is also likely that including infusion ports along the length of the device decreases the likelihood that the flushing fluid will establish a preferred flow path, which would lead to nonuniform flushing. Such mechanisms may be responsible for improved flushing achieved by locating multiple infusion ports along the length of the light treatment zone, as opposed to having them at a single location. This improvement is significant in the case of vessels without branches and is particularly dramatic for vessels having branches within the vessel region to be flushed.

Although the invention has been described with reference to specific embodiments, it should be understood that various changes may be made without departing from the spirit or scope of the invention. For instance, the various features described above and shown in the drawings can be used singly or in any of various combinations. Accordingly, the disclosed examples are intended to be illustrative of the scope of the invention and are not intended to be limiting. The scope of the invention is defined as set forth in the appended claims.

The invention claimed is:

1. A light delivery catheter for inserting into a hollow body organ having target tissue and exposing the target tissue to light, the catheter comprising:

a. an elongated tubular catheter shaft having a proximal end adapted to remain substantially outside of the body organ when in use and a distal end adapted to be substantially inserted into the body organ when in use, the distal end having a light treatment zone through which light can be transmitted;

b. a light guide in the catheter shaft for transmitting light from a light source at the proximal end of the catheter shaft to the light treatment zone;

c. an occlusion balloon positioned on the distal end of the catheter shaft adjacent to the tight treatment zone;

d. an inflation lumen in the catheter shaft and in fluid communication with the occlusion balloon for delivering fluid from an inflation fluid source at the proximal end of the catheter shaft to the occlusion balloon;

e. an infusion lumen in the catheter shaft for delivering infusion fluid from an infusion fluid source at the proximal end of the catheter shaft to the light treatment zone; and f. a plurality of infusion ports formed on the light treatment zone and in fluid communication with the infusion lumen for delivering infusion fluid to the hollow body organ, wherein the plurality of infusion ports are radially distributed about the circumference of the catheter shaft at the light treatment zone and longitudinally distributed along the length of the light treatment zone.

2. The catheter of claim 1, wherein the plurality of infusion ports comprises two infusion ports positioned around the circumference of the catheter shaft at about 180 degrees of radial separation, such that the pressure of infusion fluid passing through the ports is generally equalized.

3. The catheter of claim 1, wherein the plurality of infusion ports are positioned around the circumference of the catheter shaft at intervals of about 120 degrees or less of substantially uniform radial separation, such that the pressure of infusion fluid passing through the ports is generally equalized.

4. The catheter of claim 1, wherein the optical guide is an optical fiber, the catheter further comprising a fiber lumen in the catheter shaft in which the optical fiber can be inserted and advanced to the light treatment zone.

5. The catheter of claim 1, wherein the optical guide is an optical fiber having a distal end terminating in a diffuser within the light treatment zone.

6. The catheter of claim 5, wherein the optical fiber is inserted within the inflation lumen.

7. The catheter of claim 5, further comprising a second optical fiber in the catheter shaft for detecting light emitted by the first optical fiber and transmitting the detected light to the proximal end of the catheter shaft, the second optical fiber having a distal end terminating in a diffuser-tipped fiber for light collection within the light treatment zone.

8. The catheter of claim 1, wherein the catheter shaft is translucent at the light treatment zone.

9. The catheter of claim 1, wherein the catheter shaft contains a scattering media at the light treatment zone.

10. The catheter of claim 1, further comprising a guidewire lumen extending through the catheter shaft.

11. The catheter of claim 10, further comprising an optical fiber in the catheter shaft for delivering light to the target tissue, the optical fiber having a distal end terminating in a diffuser within the light treatment zone, wherein the optical fiber is disposed within the guidewire lumen.

12. The catheter of claim 10, further comprising a rapid exchange guidewire port formed in the guidewire lumen and catheter shaft at the distal end of the catheter shaft.

13. The catheter of claim 12, wherein the rapid exchange guidewire port is positioned adjacent and proximal to the occlusion balloon.

14. The catheter of claim 12, wherein the rapid exchange guidewire port is positioned distal to the light treatment zone.

15. The catheter of claim 1, further comprising a centering balloon through which light can be transmitted, the centering balloon positioned over the light treatment zone.

16. The catheter of claim 15, wherein the inflation lumen is in fluid communication with the centering balloon and delivers fluid for inflating the centering balloon.

17. The catheter of claim 1, further comprising an angioplasty balloon through which light can be transmitted, the angioplasty balloon positioned over the light treatment zone.

18. The catheter of claim 1, wherein the occlusion balloon is distal to the light treatment zone.

19. The catheter of claim 1, wherein the occlusion balloon is proximal to the light treatment zone.

20. The catheter of claim 19, further comprising:

a. a guidewire lumen extending through the catheter shaft; and b. a perfusion port formed in the guidewire lumen and catheter shaft proximal to the occlusion balloon to provide a bypass channel for allowing fluid in the hollow body organ to pass through the guidewire channel to the distal end of the catheter shaft when the occlusion balloon is inflated.

21. The catheter of claim 1, wherein the catheter shaft further comprises a narrowing transition adjacent to the light treatment zone, the narrowing transition reducing the diameter of the catheter shaft along the light treatment zone.

22. The catheter of claim 21, wherein the infusion lumen has a constricted portion along the light treatment zone.

23. The catheter of claim 21, wherein the infusion lumen terminates at an infusion port formed along the transition of the catheter shaft.

24. A light delivery catheter for inserting into a blood vessel having a vascular wall and exposing the vascular wall to light, the catheter comprising:

a. an elongated tubular catheter shaft having a proximal end adapted to remain substantially outside of the blood vessel when in use and a distal end adapted to be substantially inserted into the blood vessel when in use, the distal end having a light treatment zone through which light can be transmitted;

b. an optical fiber in the catheter shaft for delivering light from a light source at the proximal end of the catheter shaft to the light treatment zone, the optical fiber having a distal end terminating in a diffuser within the light treatment zone;

c. an occlusion balloon positioned on the distal end of the catheter shaft proximal to the light treatment zone;

d. an inflation lumen in the catheter shaft and in fluid communication with the occlusion balloon for delivering fluid from an inflation fluid source at the proximal end of the catheter shaft to inflate the occlusion balloon;

e. an infusion lumen in the catheter shaft for delivering infusion fluid from an infusion fluid source at the proximal end of the catheter shaft to the blood vessel; and f. a plurality of infusion ports formed in the catheter shaft and infusion lumen through which infusion fluid can be delivered into the blood vessel, wherein the plurality of infusion ports are radially distributed about the circumference of the light treatment zone and longitudinally distributed along the length of the light treatment zone.

25. A light delivery catheter for inserting into a hollow body organ having target tissue and exposing the target tissue to light, the catheter comprising:

a. an elongated tubular catheter shaft having a proximal end adapted to remain substantially outside of the body organ when in use and a distal end adapted to be substantially inserted into the body organ when in use, the distal end having a light treatment zone through which light can be transmitted;

b. a light delivery optical fiber in the catheter shaft for delivering light from a light source at the proximal end of the catheter shaft to the light treatment zone, the optical fiber having a distal end terminating in the light treatment zone; and c. a light detection optical fiber in the catheter shaft for detecting light emitted by the light delivery optical fiber and transmitting the detected light to the proximal end of the catheter shaft, the light detection optical fiber having a distal end terminating in the light treatment zone;

d. a fluorescent material incorporated into the distal end of the catheter shaft to provide a fluorescent emission when exposed to light emitted from the light delivery optical fiber, whereby the fluorescent emission can be transmitted to the proximal end of the light detection optical fiber to monitor light delivery;

e. an occlusion balloon positioned on the distal end of the catheter shaft adjacent to the light treatment zone;

f. an inflation lumen in the catheter shaft and in fluid communication with the occlusion balloon for delivering fluid from an inflation fluid source at the proximal end of the catheter shaft to the occlusion balloon;

g. an infusion lumen in the catheter shaft for delivering infusion fluid from an infusion fluid source at the proximal end of the catheter shaft to the light treatment zone; and h. a plurality of infusion ports formed on the light treatment zone and in fluid communication with the infusion lumen for delivering infusion fluid to the hollow body organ, wherein the plurality of infusion ports are radially distributed about the circumference of the catheter shaft at the light treatment zone and longitudinally distributed along the length of the light treatment zone.

26. The catheter of claim 25, wherein the light delivery optical fiber comprises a diffuser tip at the distal end.

27. The catheter of claim 25, wherein the light detection optical fiber comprises a diffuser tip at the distal end.

28. The catheter of claim 25, wherein the light detection optical fiber has a proximal end adapted to remain substantially outside of the body organ when the catheter is in use and wherein the fluorescent emission has an associated fluorescent wavelength, the catheter further comprising a wavelength selective optical element at the proximal end of the light detection optical fiber to separate the fluorescent emission.

29. The catheter of claim 28, wherein the wavelength selective optical element is a narrowband filter that passes the fluorescent wavelength and rejects extraneous wavelengths.

30. The catheter of claim 25, wherein the occlusion balloon is distal to the light treatment zone.

31. The catheter of claim 25, wherein the occlusion balloon is proximal to the light treatment zone.

32. A light delivery catheter for inserting into a hollow body organ having target tissue and exposing the target tissue to light, the catheter comprising:

a. an elongated tubular catheter shalt having a proximal end adapted to remain substantially outside of the body organ when in use and a distal end adapted to be substantially inserted into the body organ when in use, the distal end having a light treatment zone through which light can be transmitted;

b. an optical fiber in the catheter shaft for delivering light from a light source at the proximal end of the catheter shaft to the light treatment zone, the optical fiber having a distal end terminating the light treatment zone; and c. a fluorescent material incorporated into the distal end of the catheter shaft to provide a fluorescent emission when exposed to light emitted from the optical fiber, whereby the fluorescent emission can propagate back to the proximal end of the optical fiber to allow monitoring of light delivery;

d. an occlusion balloon positioned on the distal end of the catheter shaft adjacent to the light treatment zone;

e. an inflation lumen in the catheter shaft and in fluid communication with the occlusion balloon for delivering fluid from an inflation fluid source at the proximal end of the catheter shaft to the occlusion balloon;

f. an infusion lumen in the catheter shaft for delivering infusion fluid from an infusion fluid source at the proximal end of the catheter shaft to the light treatment zone; and g. a plurality of infusion ports formed on the light treatment zone and in fluid communication with the infusion lumen for delivering infusion fluid to the hollow body organ, wherein the plurality of infusion ports are radially distributed about the circumference of the catheter shaft at the light treatment zone and longitudinally distributed along the length of the light treatment zone.

33. The catheter of claim 32, wherein the optical fiber has a proximal end adapted to remain substantially outside of the body organ when the catheter is in use and wherein the fluorescent emission has an associated fluorescent wavelength, the catheter further comprising a wavelength selective optical element at the proximal end of the light detection optical fiber to separate the fluorescent wavelength.

34. The catheter of claim 33, wherein the light detection wavelength selective optical element comprises a dichroic beam splitter.

35. The catheter of claim 32, wherein the occlusion balloon is distal to the light treatment zone.

36. The catheter of claim 32, wherein the occlusion balloon is proximal to the light treatment zone.

37. A light delivery catheter for inserting into a hollow body organ having target tissue and exposing the target tissue to light, the catheter comprising:

a. an elongated tubular catheter shaft having a proximal end adapted to remain substantially outside of the body organ when in use and a distal end adapted to be substantially inserted into the body organ when in use, the distal end having a light treatment zone through which light can be transmitted, the catheter shaft having a variable diameter which forms a narrowing transition portion adjacent to the light treatment zone, the transition portion reducing the diameter of the catheter shaft along the light treatment zone;

b. a light guide in the catheter shaft for transmitting light from a light source at the proximal end of the catheter shaft to the light treatment zone;

c. an infusion lumen in the catheter shaft for delivering infusion fluid from an infusion fluid source at the proximal end of the catheter shaft to the hollow body organ, the infusion lumen having a variable diameter, wherein the diameter of the infusion lumen decreases at the transition portion of the catheter shaft; and d. one or more infusion ports formed in the catheter shaft and in fluid communication with the infusion lumen through which infusion fluid can be delivered into the hollow body organ.

38. The catheter of claim 37, further comprising:
- e. an occlusion balloon positioned on the distal end of the catheter shaft proximal to the light treatment zone; and
- f. an inflation lumen in the catheter shaft and in fluid communication with the occlusion balloon for delivering fluid from an inflation fluid source at the proximal end of the catheter shaft to the occlusion balloon.

39. A light delivery catheter for inserting into a hollow body organ having target tissue and exposing the target tissue to light, the catheter comprising:
- a. an elongated tubular catheter shaft having a proximal end adapted to remain substantially outside of the body organ when in use and a distal end adapted to be substantially inserted into the body organ when in use, the distal end having a light treatment zone through which light can be transmitted, the catheter shaft having a variable diameter which forms a narrowing transition portion adjacent to the light treatment zone, the transition portion reducing the diameter of the catheter shaft along the light treatment zone;
- b. a light guide in the catheter shaft for transmitting light from a light source at the proximal end of the catheter shaft to the light treatment zone;
- c. an infusion lumen in the catheter shaft for delivering infusion fluid from an infusion fluid source at the proximal end of the catheter shaft to the hollow body organ, the infusion lumen terminating at the transition portion of the catheter shaft; and
- d. a plurality of infusion ports formed on or near the transition portion of the catheter shaft and in fluid communication with the infusion lumen through which infusion fluid can be delivered into the hollow body organ.

40. The light delivery catheter of claim 39, wherein the infusion lumen terminates in an infusion port located on the transition portion of the catheter shaft.

41. The catheter of claim 39, further comprising:
- e. an occlusion balloon positioned on the distal end of the catheter shaft proximal to the light treatment zone; and
- f. an inflation lumen in the catheter shaft and in fluid communication with the occlusion balloon for delivering fluid from an inflation fluid source at the proximal end of the catheter shaft to the occlusion balloon.

* * * * *